US011484632B2

(12) United States Patent
Shtul

(10) Patent No.: US 11,484,632 B2
(45) Date of Patent: Nov. 1, 2022

(54) COLON CLEANING DEVICES AND METHODS

(71) Applicant: Motus GI Medical Technologies Ltd., Tirat HaCarmel (IL)

(72) Inventor: Boris Shtul, Kiryat-Yam (IL)

(73) Assignee: Motus GI Medical Technologies Ltd., Tirat HaCarmel (IL)

( * ) Notice: Subject to any disclaimer, the term of this patent is extended or adjusted under 35 U.S.C. 154(b) by 809 days.

(21) Appl. No.: 16/101,561

(22) Filed: Aug. 13, 2018

(65) Prior Publication Data

US 2018/0344907 A1 Dec. 6, 2018

Related U.S. Application Data

(62) Division of application No. 15/107,145, filed as application No. PCT/IL2014/051101 on Dec. 16, 2014, now abandoned.

(Continued)

(51) Int. Cl.
*A61M 1/00* (2006.01)
*A61M 3/02* (2006.01)
(Continued)

(52) U.S. Cl.
CPC ......... *A61M 1/0058* (2013.01); *A61B 1/0014* (2013.01); *A61B 1/00087* (2013.01);
(Continued)

(58) Field of Classification Search
CPC .... A61M 1/0058; A61M 1/00; A61M 3/0254; A61M 3/0279; A61M 3/0287;
(Continued)

(56) References Cited

U.S. PATENT DOCUMENTS 2,157,756 A * 5/1939 Irwin ................... A61M 3/0216
604/35
4,190,059 A * 2/1980 Holt ................... A61B 10/0038
604/27
(Continued)

FOREIGN PATENT DOCUMENTS

EP 1593375 11/2005
EP 2862593 4/2015
(Continued)

OTHER PUBLICATIONS

European Search Report and the European Search Opinion dated Feb. 18, 2019 From the European Patent Office Re. Application No. 18203514.7. (13 Pages).
(Continued)

*Primary Examiner* — Nicholas J. Weiss
*Assistant Examiner* — Gabriella E Burnette

(57) ABSTRACT

There is provided a colon cleaning device comprising: a tube through which liquid and fecal matter are removed from a colon of a patient, the tube having a longitudinal axis; a cleaning head positioned at the distal end of the tube, the cleaning head having at least one opening coaxial with the longitudinal axis, the at least one opening sized for fecal matter to enter the interior of the cleaning head from the colon; at least one disassembly element disposed within the cleaning head; and an actuating mechanism which actuates the disassembly element to perform sweeping displacement inside the cleaning head so that the at least one disassembly element rotates around the longitudinal axis to slice through the fecal matter; wherein the cleaning head and the tube are sized and shaped to be displaced along the colon of a patient.

8 Claims, 17 Drawing Sheets

Related U.S. Application Data

(60) Provisional application No. 61/919,765, filed on Dec. 22, 2013.

(51) Int. Cl.

| | | |
|---|---|---|
| *A61B 1/00* | (2006.01) | |
| *A61M 3/00* | (2006.01) | |
| *A61B 1/12* | (2006.01) | |
| *A61B 1/015* | (2006.01) | |
| *A61B 1/31* | (2006.01) | |
| *A61B 17/22* | (2006.01) | |

(52) U.S. Cl.
CPC ...... *A61B 1/00091* (2013.01); *A61B 1/00101* (2013.01); *A61B 1/00131* (2013.01); *A61B 1/015* (2013.01); *A61B 1/12* (2013.01); *A61B 1/126* (2013.01); *A61B 1/31* (2013.01); *A61M 1/00* (2013.01); *A61M 3/005* (2013.01); *A61M 3/0208* (2014.02); *A61M 3/0233* (2013.01); *A61M 3/0254* (2013.01); *A61M 3/0279* (2013.01); *A61M 3/0287* (2013.01); *A61B 2017/22037* (2013.01); *A61M 2202/02* (2013.01); *A61M 2202/0225* (2013.01); *A61M 2202/068* (2013.01); *A61M 2210/106* (2013.01); *A61M 2210/1064* (2013.01); *A61M 2210/1067* (2013.01)

(58) Field of Classification Search
CPC ................ A61M 3/0208; A61M 3/005; A61M 2210/1067; A61M 2210/106; A61M 2210/02; A61M 2210/068; A61M 2210/0225; A61M 2210/1064; A61B 1/015; A61B 1/12; A61B 1/126; A61B 1/31; A61B 1/00091; A61B 1/00131; A61B 1/0014; A61B 1/00101; A61B 1/00087; A61B 2017/22037
See application file for complete search history.

(56) References Cited

U.S. PATENT DOCUMENTS

| | | | |
|---|---|---|---|
| 2005/0256464 A1* | 11/2005 | Pallas | A61M 1/842 604/319 |
| 2006/0034939 A1* | 2/2006 | Kunogi | A61M 3/005 604/500 |
| 2007/0244353 A1 | 10/2007 | Larsen | |
| 2008/0004647 A1 | 1/2008 | To et al. | |
| 2008/0249553 A1 | 10/2008 | Gruber et al. | |
| 2011/0105845 A1 | 5/2011 | Gordon et al. | |
| 2012/0101336 A1 | 4/2012 | Hirsch et al. | |
| 2012/0157766 A1 | 6/2012 | Jaffery et al. | |
| 2012/0289892 A1* | 11/2012 | Shtul | A61B 1/31 604/28 |
| 2012/0289910 A1* | 11/2012 | Shtul | A61B 1/31 604/266 |
| 2013/0172680 A1* | 7/2013 | Polyakov | A61B 1/015 600/156 |
| 2017/0087284 A1 | 3/2017 | Shtul | |

FOREIGN PATENT DOCUMENTS

| | | |
|---|---|---|
| JP | 2007-160175 | 6/2007 |
| JP | 2008-000685 | 1/2008 |
| JP | 2009-533171 | 9/2009 |
| JP | 2010-246849 | 11/2010 |
| JP | 2011-520567 | 7/2011 |
| JP | 2012-085860 | 5/2012 |
| JP | 2013-516300 | 5/2013 |
| JP | 2013-532023 | 8/2013 |
| WO | WO 2004/052338 | 6/2004 |
| WO | WO 2009/095915 | 8/2009 |
| WO | WO-2009095915 A1 * | 8/2009 ......... A61B 1/00101 |
| WO | WO 2009/143201 | 11/2009 |
| WO | WO 2011/083450 | 7/2011 |
| WO | WO 2011/158232 | 12/2011 |
| WO | WO-2011158232 A2 * | 12/2011 .......... A61M 3/0208 |
| WO | WO 2013/122125 | 8/2013 |
| WO | WO 2013/187407 | 12/2013 |
| WO | WO 2015/092790 | 6/2015 |

OTHER PUBLICATIONS

Official Action dated Oct. 17, 2018 From the Re. U.S. Appl. No. 15/107,145. (17 pages).
Advisory Action Before the Filing of An Appeal Brief dated Aug. 20, 2019 From the Re. U.S. Appl. No. 15/107,145. (4 pages).
Official Action dated Apr. 29, 2019 From the Re. U.S. Appl. No. 15/107,145. (16 pages).
Glenn Elert "The Physics Hypertextbook", retrieved from Viscosity, 14 Pages, 1998.
Notice of Reason for Rejection dated Sep. 23, 2020 From the Japan Patent Office Re. Application No. 2019-028367 and Its Translation Into English. (8 Pages).
Communication Pursuant to Article 94(3) EPC dated May 7, 2020 From the European Patent Office Re. Application No. 18203514.7. (12 Pages).
Final Official Action dated May 15, 2020 from the Re. U.S. Appl. No. 15/107,145. (15 pages).
Communication Relating to the Results of the Partial International Search dated Mar. 19, 2015 From the International Searching Authority Re. Application No. PCT/IL2014051101.
International Preliminary Report on Patentability dated Jul. 7, 2016 From the International Bureau of WIPO Re. Application No. PCT/IL2014051101.
International Search Report and the Written Opinion dated May 10, 2015 From the International Searching Authority Re. Application No. PCT/IL2014051101.
Notice of Reasons for Rejection dated Jul. 31, 2018 From the Japan Patent Office Re. Application No. 2016-537540 an Its Translation Into English. (9 Pages).
Restriction Official Action dated Jun. 28, 2018 From the Re. U.S. Appl. No. 15/107,145. (7 pages).
Supplementary European Search Report and the European Search Opinion dated Sep. 11, 2017 From the European Patent Office Re. Application No. 14870803.5. (4 Pages).
Official Action dated Oct. 31, 2019 From the Re. U.S. Appl. No. 15/107,145. (13 pages).
Alkhalidi et al. "Factors Affecting Fine Bubble Creation and Bubble Size for Activated Sludge", Water and Environment Journal, 29(1): 105-113, Mar. 2015.
Notice of Reasons for Rejection dated Feb. 12, 2020 From the Japan Patent Office Re. Application No. 2019-028367 and Its Translation Into English. (10 Pages).
Notice of Reason(s) for Rejection dated May 18, 2021 From the Japan Patent Office Re. Application No. 2019-028367 and Its Translation Into English. (7 Pages).
Summons to Attend Oral Proceedings Pursuant to Rule 115(1) EPC Dated Apr. 26, 2021 From the European Patent Office Re. Application No. 18203514.7. (12 Pages).

* cited by examiner

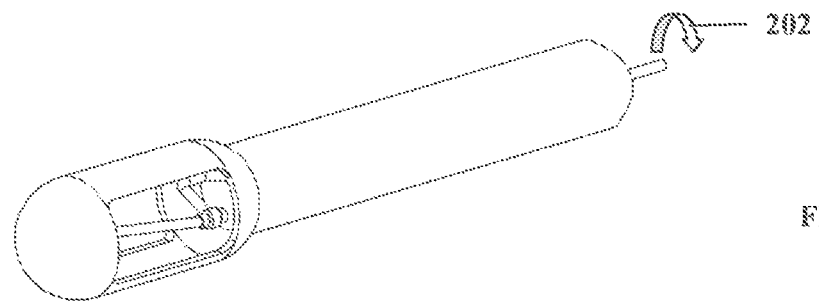
FIG. 2B
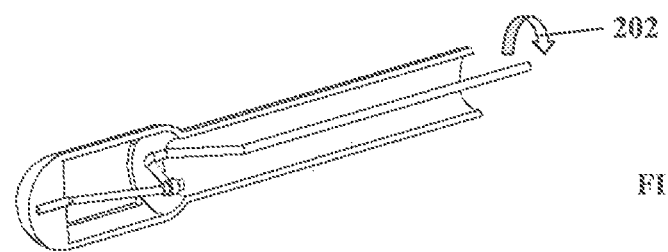
FIG. 2C
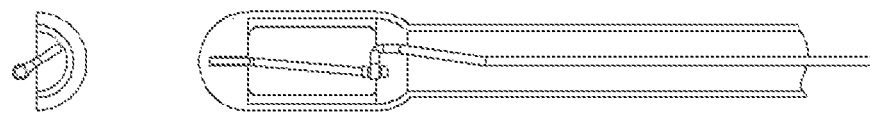
FIG. 2D
FIG. 2F
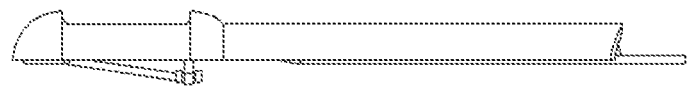
FIG. 2E

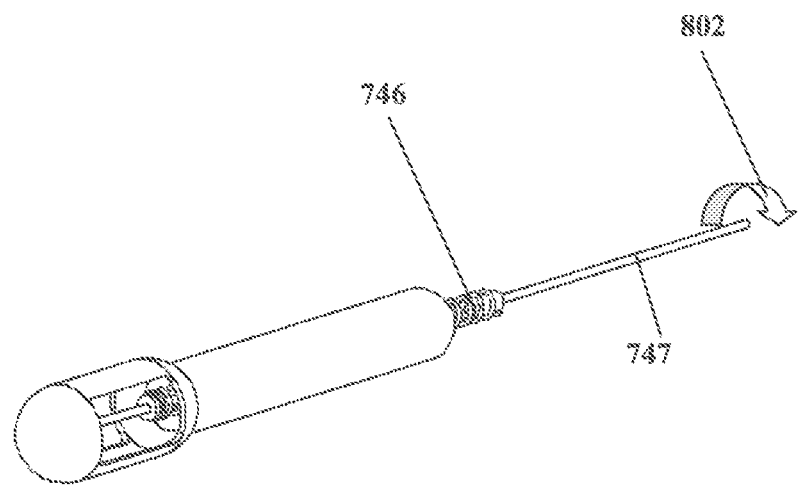
FIG. 8A
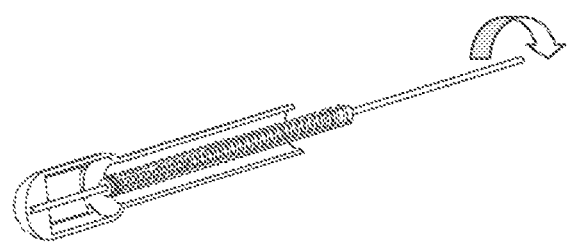
FIG. 8B
FIG. 8D  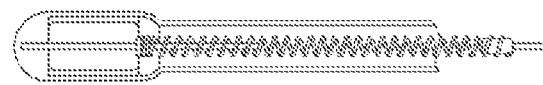
FIG. 8C
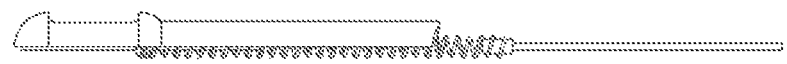
FIG. 8E

COLON CLEANING DEVICES AND METHODS

RELATED APPLICATIONS

This application is a division of U.S. patent application Ser. No. 15/107,145 filed on Jun. 22, 2016, which is a National Phase of PCT Patent Application No. PCT/IL2014/051101 having International Filing Date of Dec. 16, 2014, which claims the benefit of priority under 35 USC § 119(e) of U.S. Provisional Patent Application No. 61/919,765 filed on Dec. 22, 2013. The contents of the above applications are all incorporated by reference as if fully set forth herein in their entirety.

FIELD AND BACKGROUND OF THE PRESENT INVENTION

The present invention, in some embodiments thereof, relates to devices and methods for cleaning body cavities and, more particularly, but not exclusively, to devices and methods for cleaning a human colon.

Colonoscopy procedures have become relatively common, for example, for screening for colon cancer. In order to visualize the internal wall of the colon clearly, the fecal matter in the colon needs to be removed. Patients are prescribed a regimen of laxatives to empty out the colon before the procedure. The preparation, however, may not be complete, leaving fecal matter inside the colon that may obstruct full view of the internal colon.

Various devices and methods have been described for removing remaining fecal matter, which may be hiding a cancerous growth from view.

International Patent Application Publication No. WO 2011/158232 describes "presents methods and devices for continuously cleaning a colon by at least partially filling a segment of the colon with liquid and agitating the fluid to dislodge matter adhering to the colon walls. Methods for automatic maintenance of liquid levels in the colon during continuous cleaning are taught."

Additional background art includes:
U.S. Patent Application Publication No. US 2012/0289892;
U.S. Patent Application Publication No. US 2012/0289910;
International Patent Application Publication No. WO 2009/095915;
U.S. Patent Application Publication No. 2005/0256464.

The contents of the above applications are all incorporated by reference as if fully set forth herein in their entirety.

SUMMARY OF THE INVENTION

An aspect of some embodiments of the present invention relates to a colon cleaning device with one or more of the following features: one or more disassembly elements having sweeping motion for slicing fecal matter, a linear actuator for slidable attachment of the cleaning device to a colonoscope, a stopper for preventing possibly harmful distal motion of a shredding spring, and/or a jethead arranged to contact a partial outer circumference of the colonoscope. In exemplary embodiments, the colon cleaning device is sized and shaped to be advanced inside a human colon (optionally through the anal sphincter), while attached to the colonoscope.

According to an aspect of some embodiments of the present invention there is provided a colon cleaning device comprising: a tube through which liquid and fecal matter are removed from a colon of a patient, the tube having a longitudinal axis; a cleaning head positioned at the distal end of the tube, the cleaning head having at least one opening coaxial with the longitudinal axis, the at least one opening sized for fecal matter to enter the interior of the cleaning head from the colon; at least one disassembly element disposed within the cleaning head; and an actuating mechanism which actuates the disassembly element to perform sweeping displacement inside the cleaning head so that the at least one disassembly element rotates around the longitudinal axis to slice through the fecal matter; wherein the cleaning head and the tube are sized and shaped to be displaced along the colon of a patient.

According to some embodiments of the present invention, the disassembly element takes up a relatively small volume of space so more room is left for waste fluid and fecal matter to enter the device head for removal.

According to some embodiments of the present invention, the at least one disassembly element is a thin rod for slicing through the fecal matter during rotation around the longitudinal axis. Optionally, the rod is arranged so that the proximal and distal ends of the rod are coupled along the longitudinal axis, and a portion of the rod rotates parallel to the longitudinal axis, at a radial distance away from the longitudinal axis, between the longitudinal axis and the circumference of the cleaning head. Optionally, the rod is coupled at one end along the longitudinal axis and at the other end at a radial distance away from the longitudinal axis, so that the rod is arranged at an angle relative to the longitudinal axis.

According to some embodiments of the present invention, the at least one disassembly element is arranged so that at least a portion of the at least one disassembly element rotates at a radial distance away from the longitudinal axis so that a gap is formed between the portion and the longitudinal axis and so that another gap is formed between the portion and the interior wall of the cleaning head.

According to some embodiments of the present invention, the at least one disassembly element is coupled by at least one bearing to a power delivery mechanism for delivering torque to rotate the at least one disassembly element, so that the at least one disassembly element rotates at least partially independently of the power delivery mechanism.

According to some embodiments of the present invention, the device further comprises a stopping element coupled to the at least one disassembly element, the stopping element arranged to restrict the extent of the sweeping motion of the disassembly element, thereby preventing a portion of the at least one disassembly element from exiting the openings and damaging the colon wall.

According to some embodiments of the present invention, the cleaning head comprises two spaced apart openings arranged approximately opposite one another so that fluid and fecal matter in the intestine are able to flow in and out of the cleaning head.

According to some embodiments of the present invention, the at least one opening is positioned so that the at least one opening faces a wall of the colon when inside a relatively straight portion of the colon of the patient.

According to some embodiments of the present invention, the tube is an add-on to a colonoscope, the tube being sized to fit into the colon through an anal sphincter of a patient when coupled to the colonoscope.

According to an aspect of some embodiments of the present invention there is provided a device for coupling a colon cleaning mechanism to a colonoscope, the device comprising: a first coupling element for coupling to a distal end portion of a colonoscope, so that the coupling element remains in a stationary position relative to a longitudinal axis of the colonoscope; a second coupling element for coupling to a colon cleaning device; and a linear actuator arranged for relative linear displacement of the colon cleaning device relative to the colonoscope, in a direction coaxial to the longitudinal axis of the colonoscope; wherein the coupling device is sized and shaped to be displaced along a colon of a patient when attached to the colonoscope and to the colon cleaning device.

According to some embodiments of the present invention, the device further comprises a third coupling element arranged for slidable attachment to the distal end of the colonoscope, so that the third coupling element is simultaneously displaced with the colon cleaning device.

According to some embodiments of the present invention, the device further comprises a cable coupled to the third coupling element, the cable extending outside of the body of the patient; and a jacket coaxial with the cable, the jacket coupled to the first coupling element, the jacket extending outside of the body of the patient; wherein linear displacement of the cable relative to the jacket linearly displaces the third coupling element along the distal end portion of the colonoscope.

According to some embodiments of the present invention, the linear actuator is arranged for a displacement distance of about 10-15 centimeters.

According to some embodiments of the present invention, the first coupling element is attached proximally to a steering segment of the colonoscope. Optionally, the linear actuator is arranged so that upon complete distal displacement of the linear actuator, a distal end of the colon cleaning device is disposed within about 0-5 cm of the distal end of the colonoscope.

According to an aspect of some embodiments of the present invention there is provided a device for colon cleaning comprising: a jethead having an inner surface shaped for fitting partially around the circumference of a distal end portion of a colonoscope; a plurality of jets located within the jethead, the jets arranged to spray a fluid into a colon, the plurality of jets in fluid communication with an external source of the fluid through at least one tube; and a material output tube through which liquid and fecal matter are removed, the material output tube having an inner surface shaped for fitting partially around the circumference of a portion of the colonoscope, at a location proximal to the jethead; wherein the jethead is sized and shaped so that the combined colonoscope and jethead is displaceable along the colon of a patient.

According to some embodiments of the present invention, the inner surface of the jethead is shaped for fitting around about 150-180 degrees of the distal end portion.

According to some embodiments of the present invention, a distal portion of the jethead is angled towards the center of the colonoscope.

According to some embodiments of the present invention, the plurality of jets are in fluid communication with one another and with the external source through a manifold in the jethead.

According to some embodiments of the present invention, the device further comprises a gas inlet for supplying pressurized gas to inflate the colon.

According to an aspect of some embodiments of the present invention there is provided a colon cleaning device comprising: a material output tube through which liquid and fecal matter are removed from a colon of a patient, the tube having a longitudinal axis and a cleaning head with one or more openings, the cleaning head positioned at the distal end of the tube; a flexible rod disposed within the material output tube; a rigid rod disposed along the longitudinal axis of the cleaning head; at least one spring disposed within the material output tube, the spring coupled at a proximal end thereof to the flexible rod so that the spring rotates with the flexible rod, the spring coupled at a distal end thereof to the rigid rod, the spring arranged for shredding of fecal matter during rotation thereof; and a stopper coupled to the rigid rod for preventing one or both of expansion and distal displacement of the spring out through the at least one opening, so that damage to a wall of the colon by the spring is prevented; wherein the device is sized and shaped to be displaced along the colon of a patient.

According to some embodiments of the present invention, the rigid rod is coupled to the spring with a bearing so that the spring rotates while the rod remains stationary.

According to some embodiments of the present invention, the rigid rod is coupled to the cleaning head with a bearing so that both the spring and the rigid rod rotate together.

According to some embodiments of the present invention, the rigid rod is coupled approximately to the center of the spring so that fecal matter enters the interior of the spring through a distal end of the spring.

According to some embodiments of the present invention, the at least one opening is coaxial with the longitudinal axis of the spring.

According to some embodiments of the present invention, the device is an add-on to a colonoscope.

According to an aspect of some embodiments of the present invention there is provided a colon cleaning device comprising: a tube through which liquid and fecal matter are removed from a colon of a patient, the tube having a longitudinal axis; a shredding spring disposed in the interior of the tube; a cleaning head positioned at the distal end of the tube, the cleaning head having at least one opening coaxial with the longitudinal axis, the at least one opening sized for fecal matter to enter the interior of the cleaning head from the colon, the interior of the cleaning head in fluid communication with the tube; at least one disassembly element disposed within the cleaning head; and an actuating mechanism which actuates the disassembly element to perform sweeping displacement inside the cleaning head so that the at least one disassembly element rotates around the longitudinal axis to slice through the fecal matter; wherein fecal matter sliced by the at least one disassembly element is further shredded by the spring and transported out of the colon through the tube; and wherein the cleaning head and the tube are sized and shaped to be displaced along the colon of a patient.

According to an aspect of some embodiments of the present invention there is provided a method of cleaning a colon segment of a patient comprising: administering an emulsion of a cleaning fluid and gas bubbles into a colon segment of a patient, the gas bubbles formed to have at least one preselected bubble parameter, so that the bubbles release energy to at least structurally weaken fecal matter inside the colon segment.

According to some embodiments of the present invention, the released energy occurs by bursting of the bubbles.

According to some embodiments of the present invention, the preselected bubble parameter is an average bubble size selected so that the bubbles float to the surface of the cleaning fluid and burst at the surface, the bursting releasing the energy to disassemble the fecal matter.

According to some embodiments of the present invention, the preselected bubble parameter is a ratio of gas bubbles to cleaning fluid selected so that friction is reduced between the emulsion and pipes delivering the emulsion from an external reservoir to the colon segment, thereby providing for relatively smaller pipes to be used as compared with pipes delivering cleaning fluid without the gas bubbles.

According to some embodiments of the present invention, the preselected bubble parameter is a ratio of gas bubbles to cleaning fluid selected so that gas released into the colon segment from the gas bubbles increased ambient pressure inside the colon segment so that suction of fluid and fecal matter from the colon segment through a suction tube is increased and leakage of fluid and fecal matter through the anal sphincter is decreased, as compared to cleaning without the gas bubbles having the preselected parameter. Optionally, the method further comprises automatically detecting the increased ambient pressure within the colon segment, and automatically removing the cleaning fluid and the disassembled fecal matter out of the colon segment, so that the visual field is increased during the cleaning procedure.

According to some embodiments of the present invention, the method further comprises dynamically adjusting the at least one preselected bubble parameter during the cleaning procedure according to the consistency of the fecal matter.

According to some embodiments of the present invention, the bubbles release energy to disassemble fecal matter inside the colon segment.

Unless otherwise defined, all technical and/or scientific terms used herein have the same meaning as commonly understood by one of ordinary skill in the art to which the present invention pertains. Although methods and materials similar or equivalent to those described herein can be used in the practice or testing of embodiments of the present invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the present invention can involve performing or completing selected tasks manually, automatically, or a combination thereof. Moreover, according to actual instrumentation and equipment of embodiments of the method and/or system of the present invention, several selected tasks could be implemented by hardware, by software or by firmware or by a combination thereof using an operating system.

For example, hardware for performing selected tasks according to embodiments of the present invention could be implemented as a chip or a circuit. As software, selected tasks according to embodiments of the present invention could be implemented as a plurality of software instructions being executed by a computer using any suitable operating system. In an exemplary embodiment of the present invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the present invention are herein described, by way of example only, with reference to the accompanying drawings. With specific reference now to the drawings in detail, it is stressed that the particulars shown are by way of example and for purposes of illustrative discussion of embodiments of the present invention. In this regard, the description taken with the drawings makes apparent to those skilled in the art how embodiments of the present invention may be practiced.

In the drawings:

FIGS. 2A-2F are schematic illustrations of various views of the cleaning head of FIG. 1;

FIGS. 8A-8E are schematic illustrations of various view of the cleaning head of FIG. 7A;

DESCRIPTION OF SPECIFIC EMBODIMENTS OF THE INVENTION

Figure 1:
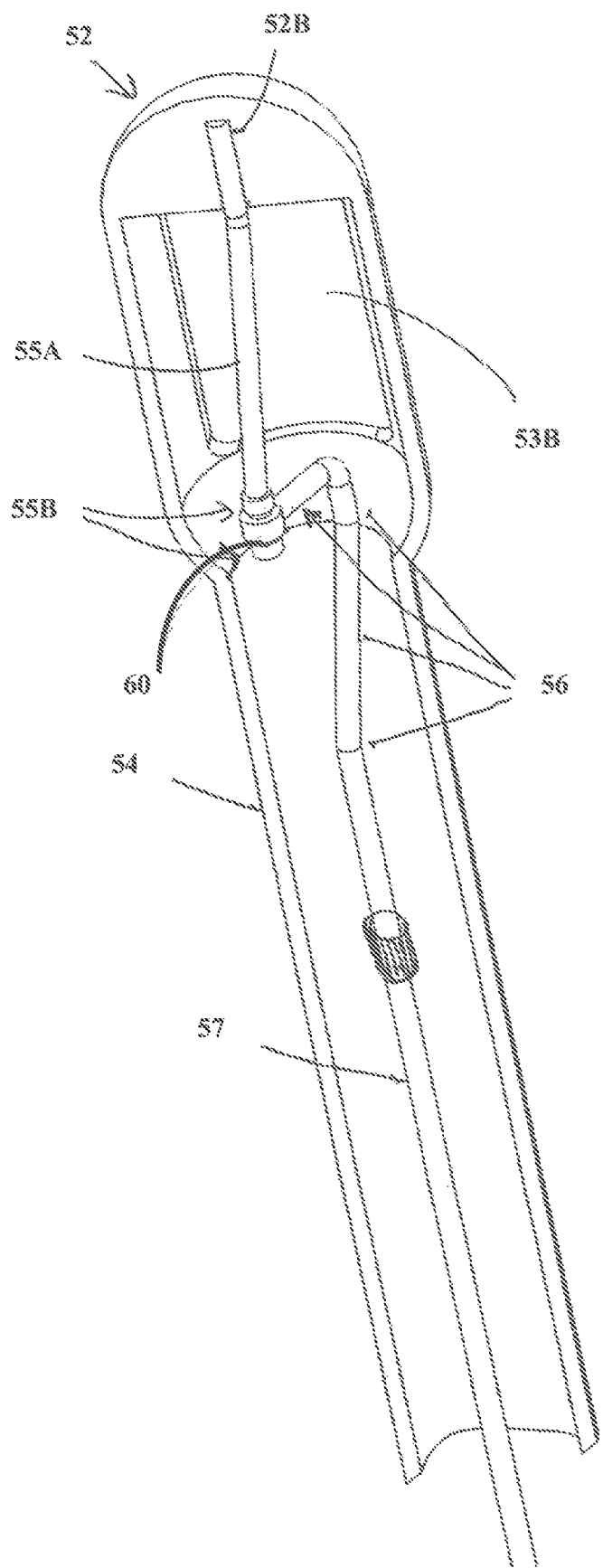
FIG. 1 is a schematic illustration of a cleaning device head having a sweeping disassembly element, in accordance with exemplary embodiments of the present invention.

The present invention, in some embodiments thereof, relates to devices and methods for cleaning body cavities and, more particularly, but not exclusively, to devices and methods for cleaning a human colon.

An aspect of some embodiments of the present invention, relates to a colon cleaning device head positioned at the end of a material removal tube, the colon cleaning device head having one or more openings for fecal matter to enter the device head, and one or more disassembly elements, such as a blade, within the colon cleaning device head for trimming and/or slicing through the fecal matter by sweeping motions inside the colon cleaning device head. Optionally, the sliced fecal matter is removed through the tube.

Optionally, the disassembly element includes a thin wire. Optionally, the thin wire takes up a relatively small volume of space so more room is left for waste fluid and fecal matter to enter the device head for removal. Optionally, the thin wire is swept through the device head to slice the fecal matter without significantly affecting flow of waste fluid and/or fecal matter out from the colon through the removal tube. Optionally, the sweeping motion of the thin wire may not create a suction force strong enough to suck the wall of the colon through openings of the device head. Optionally, the sweeping motions are retained within the cleaning device head, so that colon wall near laterally positioned openings facing the colon wall, is not damaged by the wire sweeping across the open surface of the lateral openings. Optionally, clogging of an evacuation tube by large fecal pieces is reduced or prevented by the disassembly element breaking down the large fecal pieces. Optionally, suction capacity and/or evacuation of fecal pieces is improved.

Optionally, the openings of the colon cleaning device head are arranged approximately coaxially with the longitudinal axis of the tube and/or colon cleaning device head. Optionally, when inside a relatively straight segment of colon, the openings face the colon wall. Optionally, as the material removal tube may not create a strong suction force, the colon wall is not drawn in through the openings facing the wall. Optionally, the openings facing the colon wall may improve removal of fecal matter from the colon. As patients may have already undergone preparation for a colonoscopy procedure (e.g., enema, laxatives), some of the fecal matter in the interior of the lumen of the colon may have already been removed. The remaining fecal matter may be located on the colon wall, which may be more easily removed by the openings facing the wall.

An aspect of some embodiments of the present invention relates to a coupling mechanism for coupling a colon cleaning device to a colonoscope, the coupling mechanism providing for relative displacement of the colon cleaning device relative to the colonoscope. Optionally, the relative displacement is linear. Optionally, the displacement is in a direction substantially coaxially to the longitudinal axis of the colonoscope.

Optionally, the colonoscope is held in a substantially stationary position as the coupling mechanism linearly displaces the cleaning device. Alternatively, the cleaning device is held in a substantially stationary position as the colonoscope is linearly displaced. Alternatively, both the colonoscope and the cleaning device are linearly displaced within the colon, the motion coordinated by the coupling mechanism.

Optionally, the mechanism slides the colon cleaning device to forward and/or reverse along the outer surface of the colonoscope.

Optionally, the material removal tube changes position. Optionally, the fluid injection jets do not change position. Alternatively, the fluid injection jets also change position.

As used herein, the term proximally means in a direction towards the operator of the device. For example, if the device is inside the colon, in a direction towards the anal sphincter.

As used herein, the term distal means away from the user of the device. For example, as the cleaning device is advanced forward (from the anal sphincter) inside the colon, the device is moving in a distal direction relative to the operator.

Optionally, the mechanism provides a change between two positions of the cleaning device at the distal end portion of the colonoscope. Optionally, the first position consists of the cleaning device located within about −5 centimeters (cm) to about +5 cm from the distal tip (the distal tip having a 0 reference value). Optionally, the second position consists of the cleaning device located proximally to the steering segment of the colonoscope. Optionally, the first position may allow more natural operation of the combined device as the physician may be used to operating the colonoscope in this manner. For example, control may be more predictable, as the visual sensors, the jets and the outlet tube are all at the same region at the tip. Optionally, the second position may allow easier steering, as the device does not increase the diameter and/or stiffness of the segment. Flow of injected fluid from jets at the colonoscope tip travelling backwards towards the proximally positioned evacuation tube may improve cleaning of the colon wall in the space between the jets and the tube, in addition to the region in front of the jets.

An aspect of some embodiments of the present invention relates to a jethead for supplying cleaning fluid to a colon segment, the jethead having an inner surface shaped for fitting partially around the circumference of the distal end of a colonoscope. Optionally, the jethead is sized so that the cross sectional shape and/or dimension of the combined colonoscope and jethead is small enough to be displaced along the colon of a patient, by being inserted through the anal sphincter and anal canal.

An aspect of some embodiments of the present invention relates to a colon cleaning device with one or more springs arranged for shredding fecal matter, the spring prevented from expanding and/or displacing out of the device openings by a stopper located proximally to the openings and at the distal end portion of the spring. Optionally, the stopper reduces and/or prevents the spring from damaging the colon wall.

Optionally, the spring is coupled at a distal end thereof for free rotational motion of the spring, for example, by a bearing.

Optionally, the spring is coupled approximately at the center of the distal end, so that fecal matter entry into the interior of the spring is not substantially disrupted. Fecal matter may enter between the coupling element and the inner wall of the spring.

Optionally, the central coupling may improve performance of the spring, as the spring may be rotated along the longitudinal axis of the device. Optionally, deviation of the spring to the internal wall of the device is reduced or prevented by the central coupling.

An aspect of some embodiments of the present invention relates to systems and/or methods for the administration of an emulsion composed of a cleaning fluid and gas bubbles, into a colon segment of a patient. Optionally, the gas bubbles are formed with one or more preselected bubble parameters. Optionally, the parameters are selected so that the bubbles release energy to help disassemble fecal matter inside the colon segment, for example, by at least structurally weakening the fecal matter. Alternatively or additionally, the parameters are selected so that the gas released by the bubbles increases the ambient pressure in the colon segment. Optionally, the increase in ambient pressure helps in directing waste fluid and/or fecal matter for preferential removal through a material evacuation tube. Optionally, the increase in ambient pressure reduces or prevents waste fluid and/or fecal matter from leaking out through the anal sphincter.

Alternatively or additionally, the parameters are selected so that friction between the emulsion flowing through an input tube and the walls of the input tube is relatively reduced, as compared to the friction between the cleaning fluid without the bubbles and the walls of the tube. Optionally, the input tube delivering the emulsion is designed with a relatively reduced diameter that takes into account the reduction in friction, as compared to a diameter of an input tube providing the cleaning fluid without the bubbles.

Before explaining at least one embodiment of the present invention in detail, it is to be understood that the present invention is not necessarily limited in its application to the details of construction and the arrangement of the components and/or methods set forth in the following description and/or illustrated in the drawings and/or the Examples. The present invention is capable of other embodiments or of being practiced or carried out in various ways.

Referring now to the drawings, FIG. 1 is a cross sectional side view schematic illustration of a colon cleaning head 52 for slicing through fecal matter, in accordance with exemplary embodiments of the present invention. Optionally, cleaning head 52 is disposed at the distal end of a material removal tube 54. Optionally, the disassembly element may slice fecal matter to a size small enough so that the fecal matter may be removed out of the colon through tube 54. The slicing may be performed without substantially affecting the flow removal rate of the fecal matter and/or fluid, and may increase the flow removal rate by the slicing. The slicing may be performed with reduced risk of damaging the colon wall. Optionally, the slicing is performed to reduce the size of the fecal matter so that the fecal matter may enter the interior of a shredding spring for further shredding.

Cleaning head 52 may be used alone to clean a colon, or attached to a colonoscope to clean a colon during a colonoscopy procedure.

Cleaning head 52 has one or more openings 53B. The size of opening 53B is large enough for fecal matter to enter the interior of head 52 from the colon.

Optionally, opening 53B is located coaxially with the longitudinal axis of cleaning head 52. Optionally, opening 53B faces the colon wall during a cleaning procedure. Head 52 may be designed with different numbers of openings and different arrangements of the location of the openings, for example, multiple small openings, one or two large openings, one or more openings located at the distal end of head 52 facing forwards, spaced apart openings around the circumference of head 52, or other arrangements. Optionally, the openings may be placed to improve flow through head 52.

Optionally, the openings may be placed to improve removal of feces stuck to the colon wall.

Optionally, flaps are arranged for opening and closing the lateral openings. For example, the flaps slide forward and backwards along tracks parallel to the opening.

Optionally, the flaps are manually controlled by the user and/or automatically by software.

Optionally, each flap for each opening is controlled independently. Alternatively, all the flaps for all the openings are controlled together.

Cleaning head 52 has one or more disassembly elements arranged for sweeping motion to slice through fecal matter. There may be 1, 2, 3, 5, or other number of disassembly elements and the rod connected thereto.

Optionally, the disassembly element is a thin rod 55A for slicing fecal matter during the sweeping motions. Alternatively, the disassembly element is a wire. Alternatively, the disassembly element is a blade. Alternatively, the disassembly element is a spring.

Optionally, rod 55A is made out of rigid material, for example, stainless steel. Alternatively, rod 55A is made out of flexible material, for example, nickel titanium.

The cross sectional diameter of rod 55A is, for example, about 1-3 millimeters (mm), or about 0.1-1 mm, or about 0.01-0.1 mm, or other smaller, intermediate or larger diameters.

Optionally, rod 55A is substantially circular. The slicing may be done by the thin diameter of the rod and/or by the rotational speed and/or force. Alternatively or additionally, the disassembly element (e.g., rod 55A) has a sharpened edge for slicing.

Optionally, rod 55A is coupled to an actuating mechanism arranged to rotate rod 55A around the longitudinal axis of cleaning head 52. Optionally, rod 55A is arranged so that at least a portion of rod 55A is rotated by the actuating mechanism at a radial distance away from the longitudinal axis, so that there is a gap between the rotating portion and the axis. Optionally, rod 55A is substantially straight. Alternatively or additionally, rod 55A is entirely, or contains a portion having other shapes, for example, curves, sinusoidal patterns, pointed ends, bends, or other shapes, such as 'U', 'V', 'Y', 'S', 'N', or other shapes.

Optionally, rod 55A is arranged for sweeping movements that leave a gap between rod 55A and the interior wall of cleaning head 52.

Optionally, rod 55A is arranged for sweeping motion across opening 53B. Optionally, fecal matter that is partially in head 52 and partially outside (in the colon) is cut by rod 55A.

Optionally, rod 55A is arranged at an angle relative to the long axis. The angle is, for example, about 5-15 degrees, or about 15-30 degrees, or about 30-45 degrees, or about 45-60 degrees, or about 60-89 degrees. Alternatively or additionally, one or more rods are arranged approximately parallel to the long axis (as will be shown in FIG. 3). Alternatively or additionally, one or more rods are arranged approximately perpendicular to the long axis. Optionally, the number and/or position of the rods are selected according to various parameters, for example, the hardness of the fecal matter, and/or the amount of expected fecal matter. For example, a higher number of rods arranged in different positions may be used if hard and/or large amount of feces need to be sliced. For example, the single rod may be used if smaller amounts of fecal matter are expected to be encountered.

Optionally, the cleaning head is available as a part of a kit, in different configurations, for example, with different numbers and/or orientations of rods and/or other disassembly elements, for example, for different patients and/or different cleaning scenarios. Optionally, head is removable from tube, and/or replaceable, for example, using threads.

Optionally, the distal end of rod 55A is coupled to the distal end of head 52 at coupling location 52B. Optionally, the coupling is rigid at location 52B, for example, using welding, glue, a press nut, or other suitable methods. Optionally, in this case, rod 55A is made out of flexible material (e.g., Nickel titanium) so that the rest of rod 55A may be moved. Alternatively, the coupling at location 52B provides for free motion, for example, using a bearing or other suitable methods.

Optionally, the proximal end of rod 55A is coupled to a distal end of an actuating mechanism for delivering power for the sweeping motion of rod 55A, for example, rotational motion and/or forward and/or reverse displacement. Optionally, the power delivery is provided by a cable 57 (e.g., attached at a proximal end thereof to an external motor).

Optionally, rod 55A is coupled to cable 57 to provide at least partial motion of rod 55A independently of cable 57, for example, using a bearing. Optionally, the distal end of cable 57 has an approximately U or C shaped arm 56. Optionally, arm 56 may provide for sweeping motions of rod 55A during use. Optionally, rod 55A is coupled to arm 56 by a bearing 60. Optionally, bearing 60 provides free motion of rod 55A relative to arm 56, forward, reverse and/or rotational. Optionally, stoppers 55B on opposite ends of bearing 60 restrict the extent of motion of rod 55A. Optionally, the risk of rod 55A advancing out of the openings to damage the colon wall is reduced or prevented by the stoppers.

Optionally, tube 54 is long enough for advancement at least as far as the sigmoid colon (through the anal sphincter), or as far as the cecum. The length is, for example, at least about 50 cm, at least about 100 cm, at least about 200 cm, or other smaller, intermediate or larger lengths.

Optionally, head 52 is sized to fit through an anal sphincter of a patient when optionally attached to a colonoscope.

Reference is now made to FIGS. 2A-2F, which are different views of the cleaning device of FIG. 1.

Figure 2A:
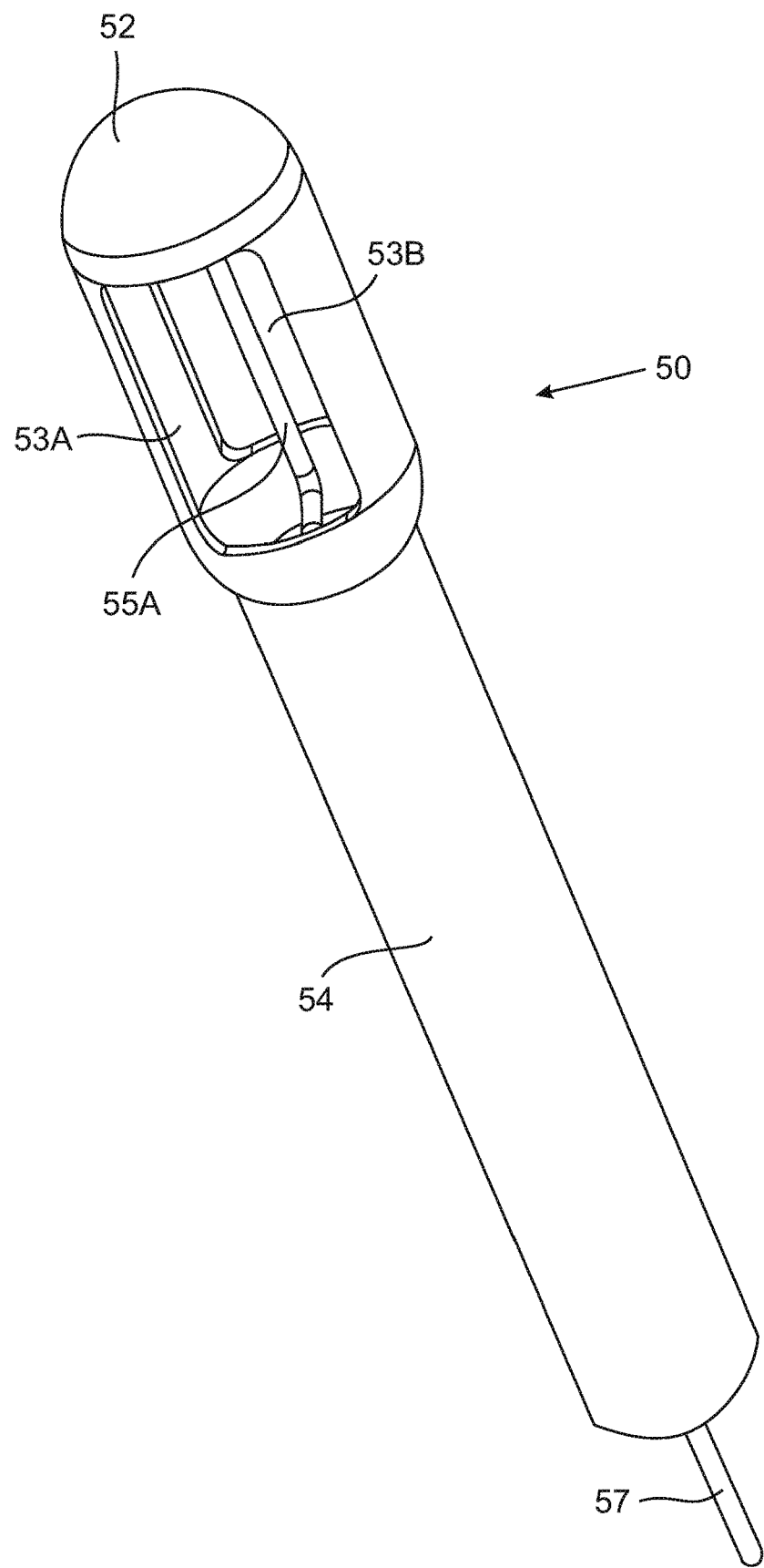

FIG. 2A is a perspective view of the cleaning head and tube of FIG. 1, having two openings 53A and 53B spaced apart along the circumference of cleaning head 52. Optionally, the two openings are located opposite one another. Rod 55A is shown after a 180 degree rotation along the long axis relative to the position shown in FIG. 1.

Optionally, head 52 and tube 54 are manufactured as a single component 50. Alternatively, head 52 and tube 54 are detachable and replaceable, for example, different types of head designs may be screwed or clicked to the tube.

FIG. 2B is a perspective view of the cleaning head and tube of FIG. 1, illustrating the direction of applied torque 202, as would be provided, for example, by an external motor. Alternatively, the torque is applied in the opposite direction to that shown. Alternatively or additionally, forward and/or reverse distal displacement is applied.

FIG. 2C is a cross sectional perspective view of the cleaning head and tube of FIG. 1, illustrating the direction of applied torque 202.

FIG. 2D is a cross sectional side view of the cleaning head and tube of FIG. 1.

FIG. 2E is a cross sectional top view of the cleaning head and tube of FIG. 1.

FIG. 2F is a cross sectional front view of the cleaning head and tube of FIG. 1.

Figure 3:
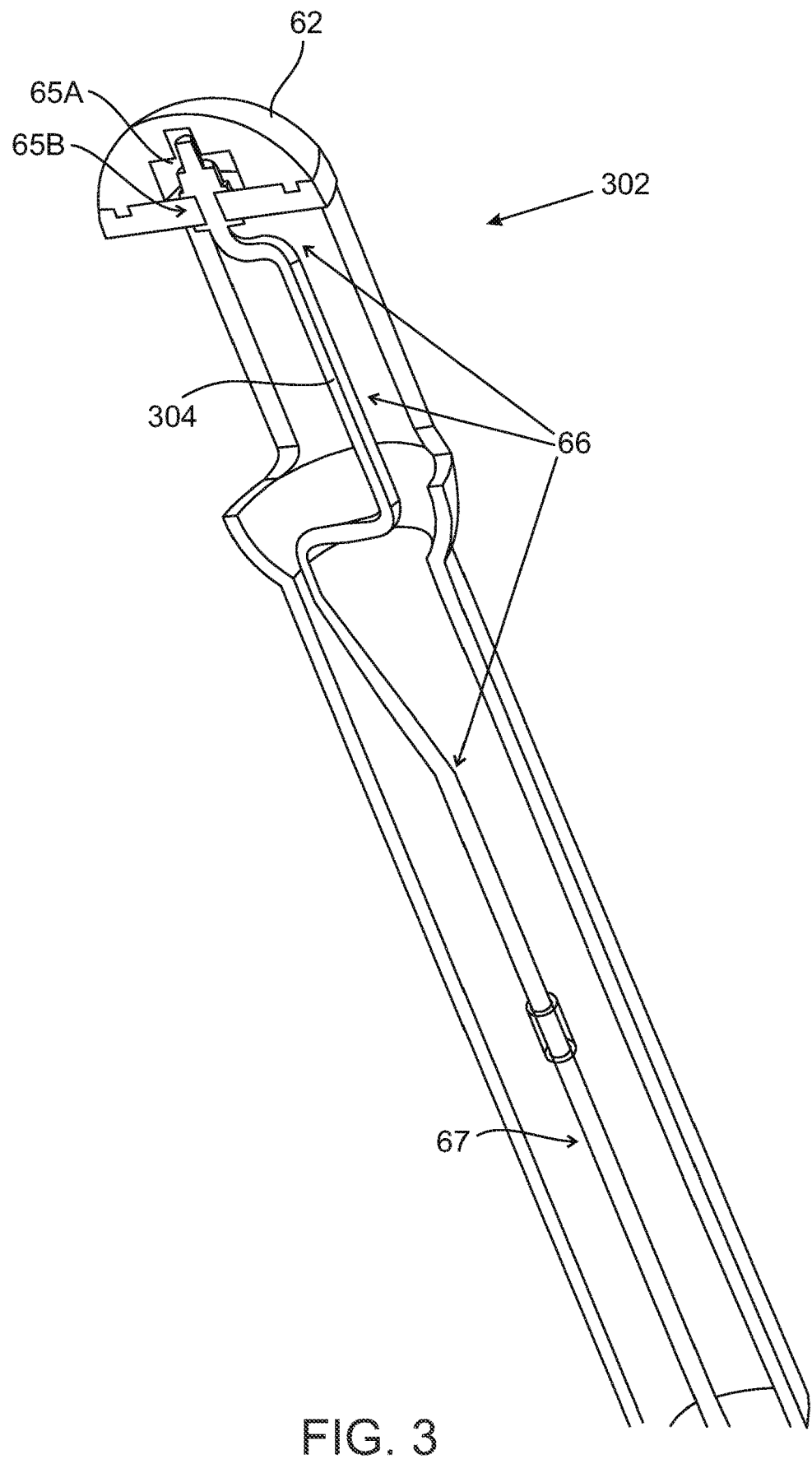
FIG. 3 is a schematic illustration of another embodiment of the cleaning head with sweeping disassembly element, in accordance with exemplary embodiments of the present invention.

Reference is now made to FIG. 3, which is another embodiment of a colon cleaning head 302 with fecal matter slicing rod, in accordance with exemplary embodiments of the present invention.

Optionally, a slicing rod 66 is rigidly coupled to a power delivery wire 67, for example, rod 66 and wire 67 are a single continuous wire, or rod 66 is attached to wire 67 by gluing, welding, crimping, or other methods.

Optionally, a portion 304 of rod 66 is arranged coaxial to, and radially spaced apart, from the longitudinal axis of the cleaning head. Optionally, portion 304 has a length suitable for sweeping across the entire open surface area of the openings of the cleaning head.

Optionally, one or more bearings 65A-B are disposed at a distal end 62 of cleaning head 302. Bearings 65A-B couple rod 66 to end 62, so that rod 66 is able to rotate along the longitudinal axis.

Optionally, rod 66 is rigid. Rod 66 is made from, for example, stainless steel.

Reference is now made to FIGS. 4A-4E, which are different views of the cleaning device of FIG. 3.

Figure 4A:
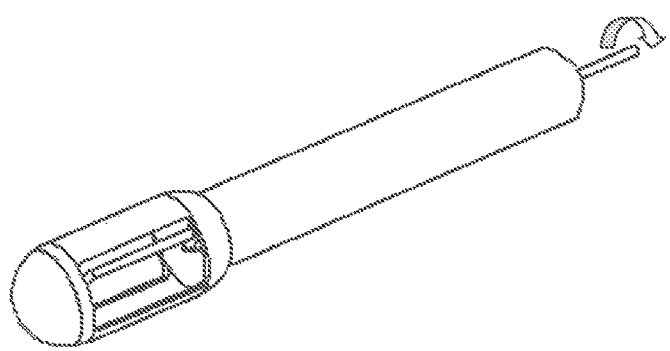
FIGS. 4A-4E are schematic illustration of various view of the cleaning head of FIG. 3.

FIG. 4A is a perspective view of the cleaning head and tube of FIG. 3.

Figure 4B:
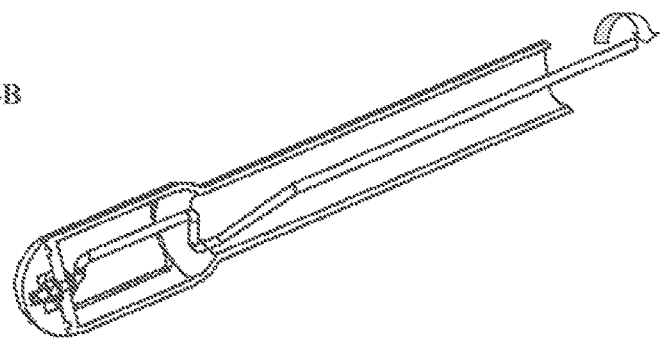

FIG. 4B is a perspective cross sectional view of the cleaning head and tube of FIG. 3.

Figure 4C:
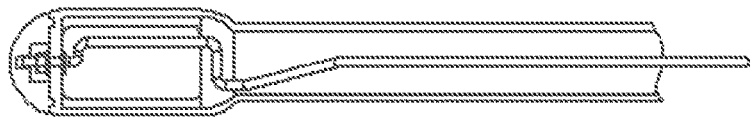

FIG. 4C is a cross sectional side view of the cleaning head and tube of FIG. 3.

Figure 4E:
Figure 4D:
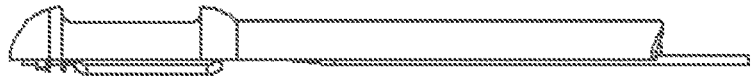

FIG. 4D is a cross sectional top view of the cleaning head and tube of FIG. 3.

FIG. 4E is a cross sectional front view of the cleaning head and tube of FIG. 3.

Figure 5A:
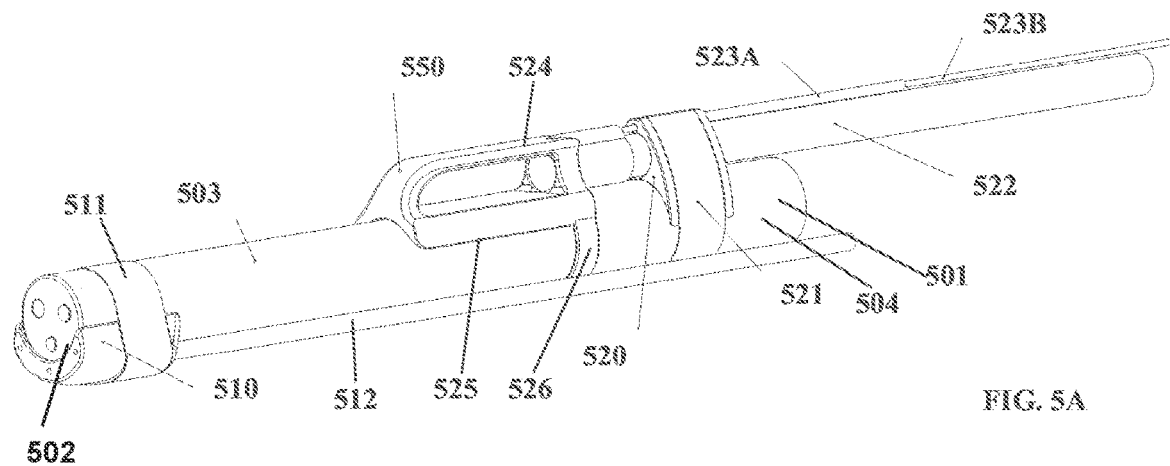
FIGS. 5A-5D are schematic illustrations of a coupling mechanism that provides for displacement of the colon cleaning device along the long axis of the colonoscope, in accordance with exemplary embodiments of the present invention.

Reference is now made to FIG. 5A, which is a schematic illustrating a device for coupling a colon cleaner 550 to a colonoscope 501 so that colon cleaner 550 is slidably displaceable along the surface of colonoscope 501, in accordance with exemplary embodiments of the present invention.

Optionally, an inner surface 525 of cleaner 550 is shaped to fit against an outer surface of colonoscope 501.

In exemplary embodiments, a linear actuator 520 couples colon cleaner 550 to colonoscope 501 and provides for motion of cleaner 550 relative to colonoscope 501. Actuator 520 has a connector for connecting to colonoscope 501 in a stationary manner. Optionally, the stationary connector is a band 521, a snap-in joint, a weld, glue, or other methods for stationary attachment.

Optionally, actuator 520 has another connector for slidably connecting to colonoscope 501, for example, a second band 526, a rail, a helical track, or other suitable connectors. Optionally, the frictional force between band 526 and colonoscope 501 is easily overcome, to allow sliding motion of band 526 during use. For example, band 526 is semi-circular and/or the radial force exerted by band 526 is weak to allow the sliding of band 526. Optionally, band 526 provides additional stability to the colon cleaner device during the sliding motion. Alternatively, no band 526 is used.

Optionally, linear motion of actuator 520 is controlled remotely from outside the body of the patient by a control mechanism. The control mechanism is, for example, a cable driver 523B coaxial with (e.g., within) a cable jacket 523A. Optionally, cable 523B is coupled to the movable component of actuator 520 (e.g., second band 526). Optionally, jacket 523A is coupled to the stationary component of actuator 520 (e.g., first band 521). Cable 523B may be displaced forward and/or reverse within stationary jacket 523A, thereby linearly displacing the movable component of actuator 520. Control may be provided, for example, by a linear actuator motor coupled to cable 523B and/or jacket 523A, and/or by the operator manually pulling and/or pushing cable 523B relative to jacket 523A. In another example, the motion of actuator 520 is controlled by a motor turning a helical track against inner threads. In yet another example, motion of actuator 520 is controlled by a motor pushing, pulling and/or rolling against a linear track.

Optionally, colon cleaner 550 is coupled to linear actuator 520 to enable linear motion of cleaner 550.

Optionally, colon cleaner 550 contains two parts, a fluid inlet for delivering cleaning fluid into the colon, and a material evacuator for removing waste from the colon.

Optionally, a jethead 510 for injection of a cleaning fluid is coupled to end portion 502 in a stationary manner, for example, using a band 511. Alternatively, jethead 510 is coupled to linear actuator 520, to provide for linear motion.

Optionally, jethead 510 is in fluid communication with an external source of the cleaning fluid through one or more fluid pipes 512.

Optionally, a material removal tube head 524 is coupled to linear actuator 520, to provide for linear motion. Alternatively, removal head 524 is stationary coupled to colonoscope 550. Head 524 is in fluid communication with an external waste reservoir through on or more matter removal tubes 522.

Colonoscope 501 optionally comprises a steering segment 503 at the distal end portion 502 thereof. In use, steering segment 503 curves in a direction under control of an operator, to navigate colonoscope 501 through the tortuous colon. The region of colonoscope 501 proximal to end portion 502 is referred to herein as an insertion tube 504.

Optionally, linear actuator 520 is located proximally to steering segment 503. For example, about 10-15 cm, or about 15-20 cm, or about 5-10 cm proximally to end 502. Optionally, linear actuator 520 is long enough to displace device 550 up to tip 502, or past tip 502, for example, a distance of about 5-10 cm, or about 10-15 cm, or about 15-20 cm, or about 20-30 cm.

As shown, cleaner 550 is located proximally to steering segment 503.

Figure 5B:
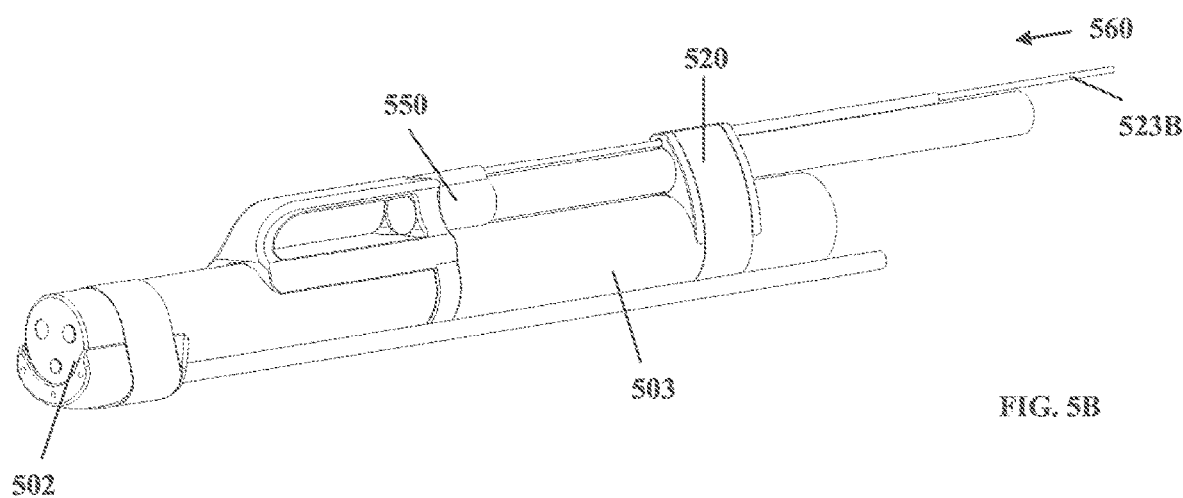

Reference is now made to FIG. 5B, which is a schematic illustrating partial distal displacement of cleaner 550 relative to colonoscope 501 from the position of FIG. 5A, using linear actuator 520. In use, cable driver 523B is distally displaced (shown by arrow 560) by the external linear actuator, distally displacing cleaner 550.

As shown, cleaner 550 is located distally to steering segment 503, and proximally to tip 502.

Figure 5C:
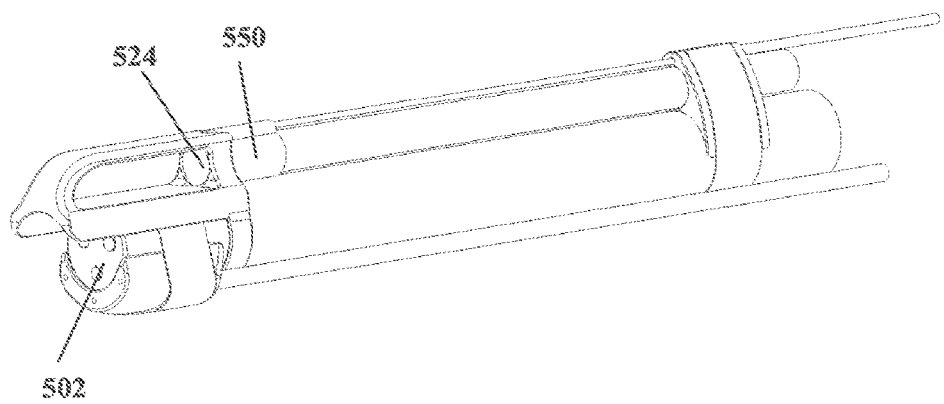

Reference is now made to FIG. 5C, which is a schematic illustrating complete distal displacement of cleaner 550 relative to colonoscope 501 from the position of FIG. 5A. Material output tube opening 524 is now located close to tip 502.

Figure 5D:
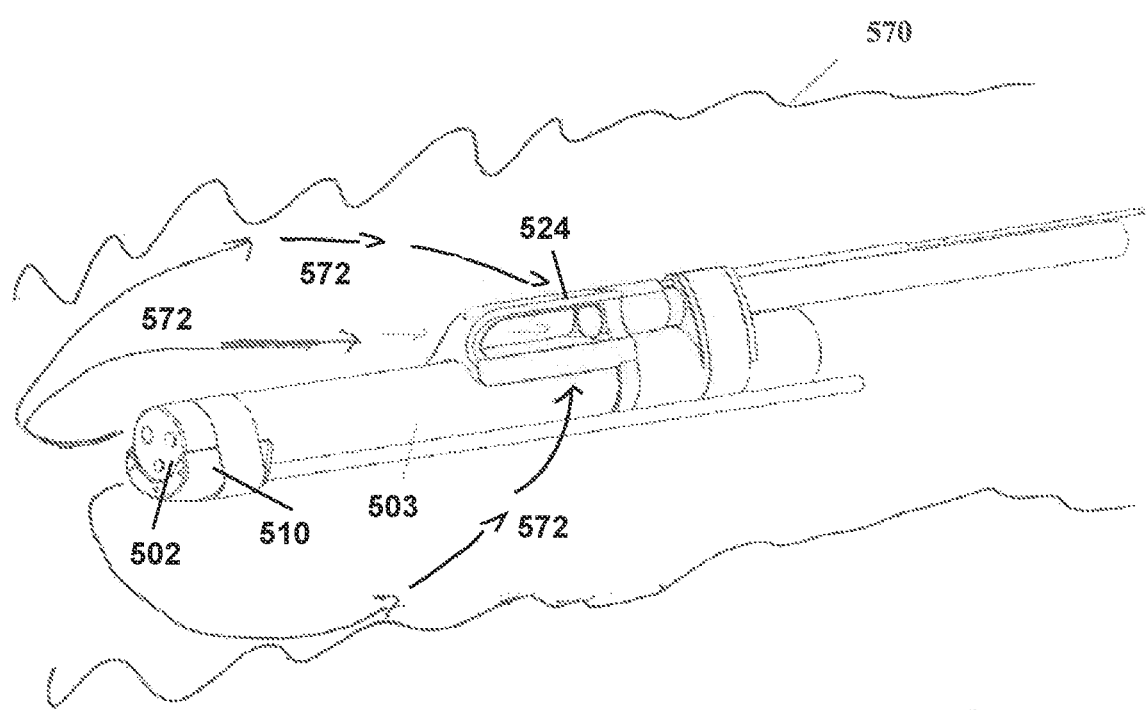

Reference is now made to FIG. 5D, which is a schematic of colon cleaner 550, linear actuator 520 and colonoscope 501 of FIG. 5A inside a colon 570. Arrows 572 illustrate flow of injected fluid from jethead 510 (located at end 502) proximally and into matter removal opening 524 located proximally to steering segment 503 (and subsequently out of the colon). Optionally, the distal to proximal fluid flow helps to improve cleaning of a colon segment in near proximity to the visual sensor of the colonoscope.

Figure 6A:
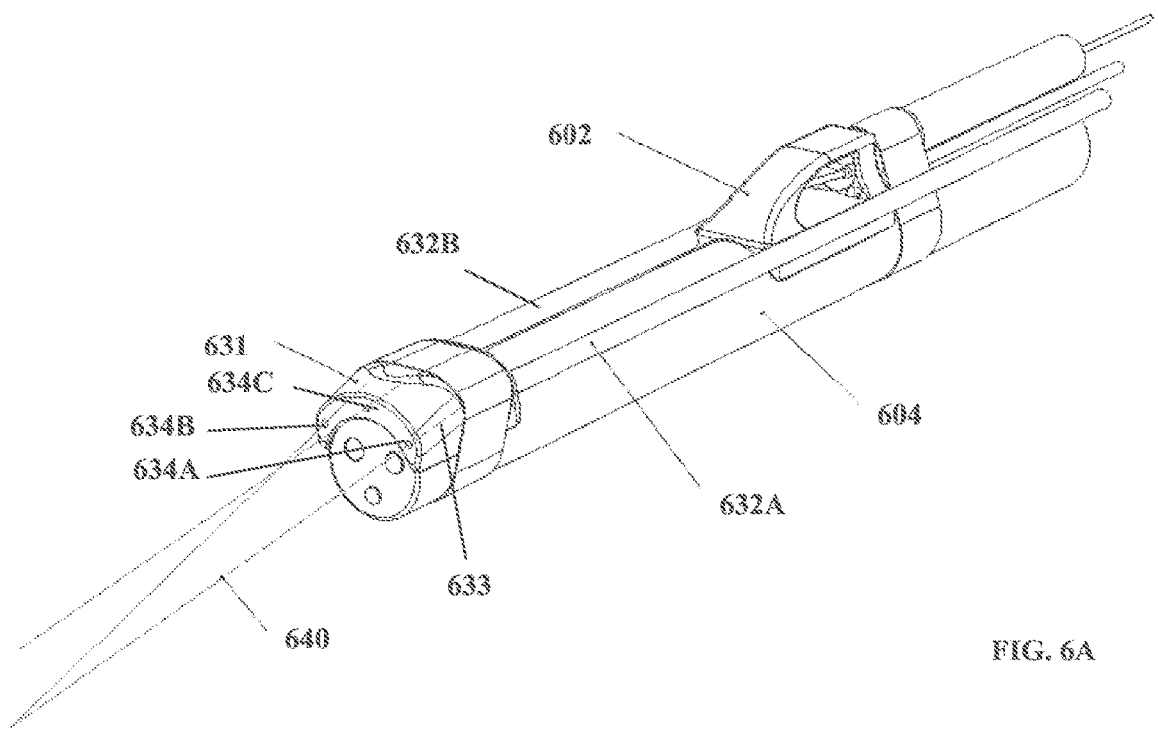
FIGS. 6A-6D are schematic illustrations of an exemplary jethead of a colon cleaning device, in accordance with exemplary embodiments of the present invention.

Reference is now made to FIG. 6A, which is a schematic of a colon cleaning device 602 having jethead 631 sized to reduce an overall diameter when coupled to a colonoscope 604, so that the combined jethead 631 and colonoscope 604 is able to enter the colon of a patient by being advanced through the anal sphincter, in accordance with exemplary embodiments of the present invention.

In exemplary embodiments, jethead 631 has an inner surface shaped for fitting partially around the external surface of the colonoscope 604, optionally around the distal end portion. The inner surface contacts, for example, about 180 degrees of the outer circumference of the end portion, or about 30-60 degrees, or about 60-90 degrees, or about 90-120 degrees, or about 120-150 degrees, or about 150-180 degrees, or about 180-210 degrees, or about 210-240 degrees, or about 240-270. Optionally, the overall diameter is reduced by only increasing a segment of the outer circumference of the colonoscope, and not the entire outer circumference.

The arc length of the inner surface may be selected, for example, according to the number of jet openings and/or according to the position of the jets. For example, in the single jet configuration, an arc length of about 30-60 degrees may be sufficient to accommodate the single jet. For example, if three jets are used, each pointing in different directions, an arc length large enough to accommodate the jet configuration may be selected, for example, about 150-180 degrees may be selected.

Jets may be arranged to achieve desired effects, for example, to swirl fluid within the colon, clean the colonoscope and/or assist in disassembling fecal matter inside the colon. For example, jets may be directed in a forward direction, to spray in front of the colonoscope. Jets may be directed outwards to spray the periphery of the colon. Jets may be directed to a focal point, or to several focal points, or so that there is no substantial focal point. Jets may be directed to cross one another. Additional details of exemplary arrangements of jets are described, for example, in International Patent Application Publication No. WO 2011/158232.

The inner surface is designed to fit snugly around colonoscopes of various diameters, for example, 13.6 millimeter (mm), 14.0 mm, 14.7 mm, or other sizes of commercially available off-the-shelf colonoscopes. Jethead 631 may be located anywhere along the outer circumference of colonoscope 604, for example, centered at about 0 o'clock (i.e., face on view), or at about 3 o'clock, or at about 6 o'clock, or at about 9 o'clock, or other intermediate locations.

One or more pipes 632A-B connect jethead 631 with the external source of cleaning fluid. Pipes 632 A-B lead into an optional manifold 633 inside jethead 631. The cleaning fluid is sprayed 640 out through one or more jet openings 634A-C. Optionally, manifold 633 places openings 634A-C in fluid communication with one another, and may equalize the pressure and/or fluid flow though openings 634A-C. Optionally, each jet opening points in a preselected direction in order to provide a spray arrangement to break down and/or dissolve fecal matter in the colon.

Figure 6B:
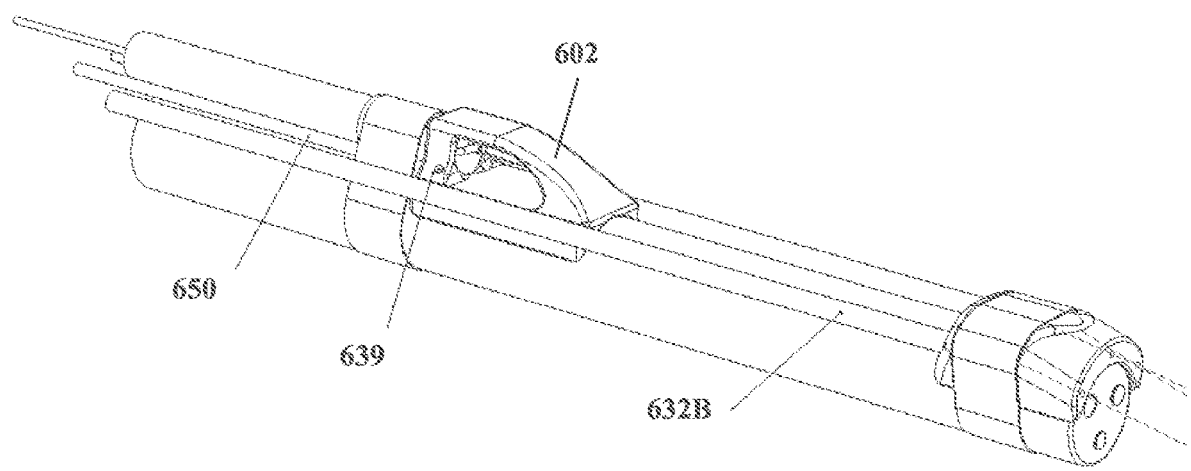

FIG. 6B is a schematic illustration of the colon cleaning device and colonoscope of FIG. 6A as viewed from the opposite direction.

Device 602 has an optional gas inlet 639 for supplying pressurized gas to inflate the colon before and/or during the cleaning procedure. Inlet 639 is in fluid communication with an external gas reservoir through one or more gas tubes 650. Examples of suitable gases include air or carbon dioxide.

Figure 6C:
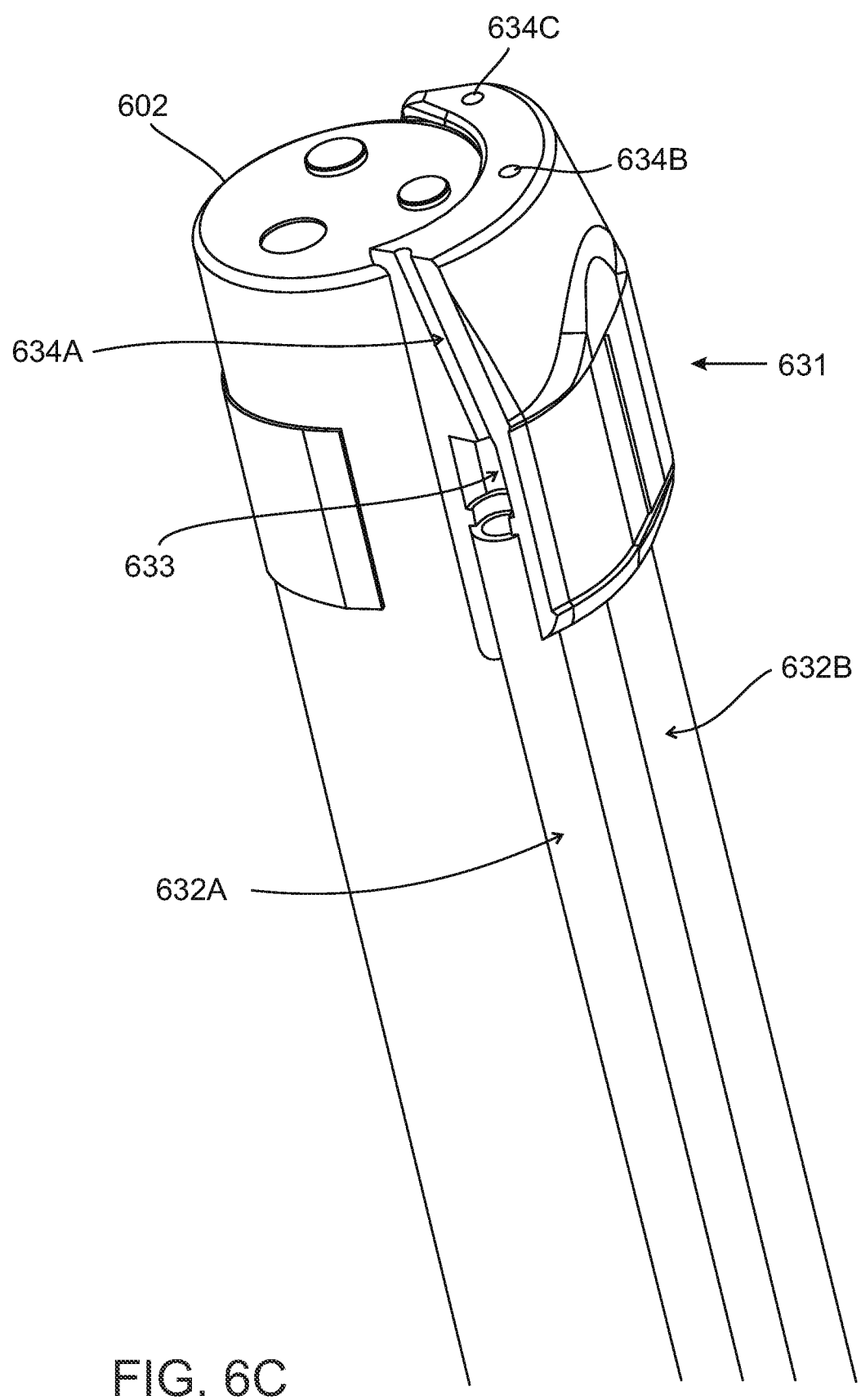

FIG. 6C is a blow up of the distal portion of the colonoscope of FIG. 6A, showing the internal manifold 633 of jethead 631.

Optionally, the distal portion of jethead 631 is angled towards the center of the colonoscope. Optionally, the angling may make it easier to pass the combined jethead 631 and colonoscope 604 through the anal sphincter and/or to navigate the colon.

Figure 6D:
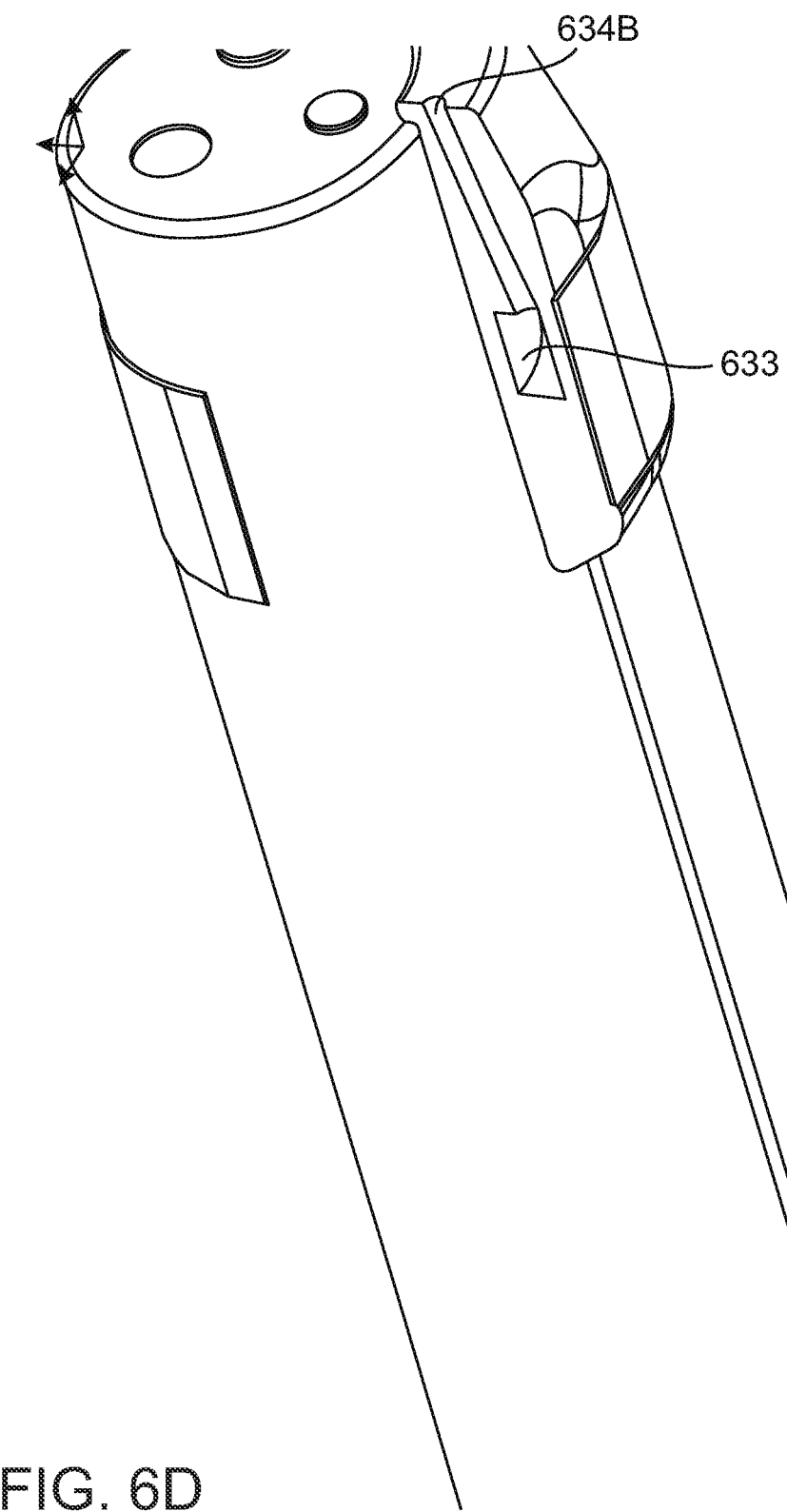

FIG. 6D is a blow up of the distal portion of the colonoscope of FIG. 6A, with a cross sectional slice through jet opening 634. Optionally, the cleaning fluid that is ejected out from jet 634B is provided by the inlet pipe, though manifold 633.

Figure 7A:
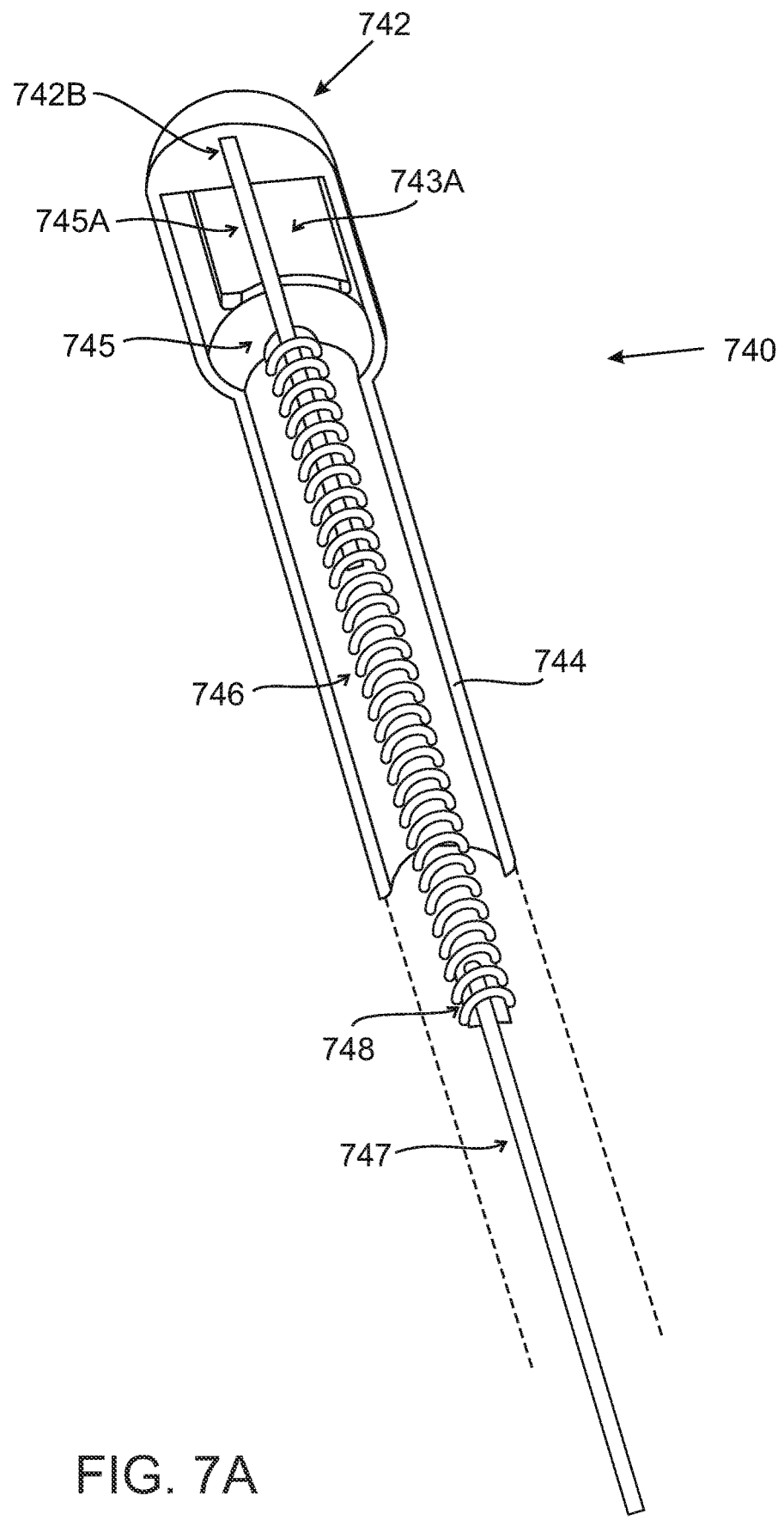
FIGS. 7A-7B are schematic illustration of an exemplary cleaning head with a fecal removal and/or shredding element, in accordance with some exemplary embodiments of the present invention.

Reference is now made to FIG. 7A, which is a schematic illustration of a colon cleaning device 740 having one or more shredding springs 746 held in position by one or more stoppers 745C. Stopper 745 is arranged to prevent or reduce spring motion (e.g., expansion and/or forward displacement during operation) out of an opening 743A of device 740. Optionally, stopper 745C prevents or reduces damage to the colon wall.

Optionally, spring 746 is arranged to shred fecal matter, for example, fecal particles are shredded during rotational movement of the inner coils. Alternatively or additionally, the rotational motion of the helically arranged coils of spring 746 helps in removal of the fecal matter out of the body.

Additional details of exemplary springs are described, for example, in U.S. Patent Application Publication No. 2012/0289892.

Spring 746 is located at a distal end of a matter evacuation tube 744 for removing fecal matter and fluids out of the colon.

A proximal end 748 of spring 746 is coupled to a distal end of a flexible rod 747 for transmitting torque from an external power source such as a motor. Optionally, spring 746 is rigidly coupled at end 748 to rod 747 so that spring 746 rotates together with rod 747. Optionally, rod 747 is located within tube 744. Optionally, rod 747 is flexible so that torque may be transmitted from outside of the body of the patient, through the tortuous colon, to spring 746.

The distal end of spring 746 is coupled to a proximal end of a rod 745A. Optionally, rod 745A is rigid to help maintain the position of spring 746. Optionally, rod 745A is arranged approximately along the long axis of device 740. Optionally, rod 745A is coupled to a distal end 742 of device 740.

Optionally, the distal end of rod 745A is rigidly coupled at location 742B (e.g., using glue, weld, tight frictional fit, and/or other suitable methods) to distal end of device 740, and the proximal end of rod 745A is coupled to the distal end of spring 746 with a bearing, so that spring 746 is able to rotate relative to stationary rod 745A. Optionally, the bearing serves as stopper 745C so that spring 746 is unable to expand and/or move distally past stopper 745C.

Alternatively, the distal end of rod 745A is freely coupled at location 742B (e.g., using a bearing or other methods) to distal end of device 740, and the proximal end of rod 745A is rigidly coupled to the distal end of spring 746, so that spring 746 rotates together with rod 745A. Optionally, the rigid coupling serves as stopper 745C.

Optionally, rod 745A maintains the distal end of the spring in an approximately coaxial position relative to the longitudinal axis of evacuation tube 744.

Optionally, a region of spring 746 between the coupled distal and proximal ends shreds the fecal matter and/or removes the fecal matter away from the distal end of device 740.

Optionally, distal end 742 of device 740 has one or more openings 743A sized for fecal matter from the colon to enter the interior of device 740. Optionally, the openings 743A are positioned coaxially to spring 746. Optionally, the parallel arrangement of the spring and the windows acts as another safety feature, reducing the risk of the spring exiting through the window to damage the colon. Additional details of different window configurations have been described herein, for example, with reference to FIG. 1.

Figure 7B:
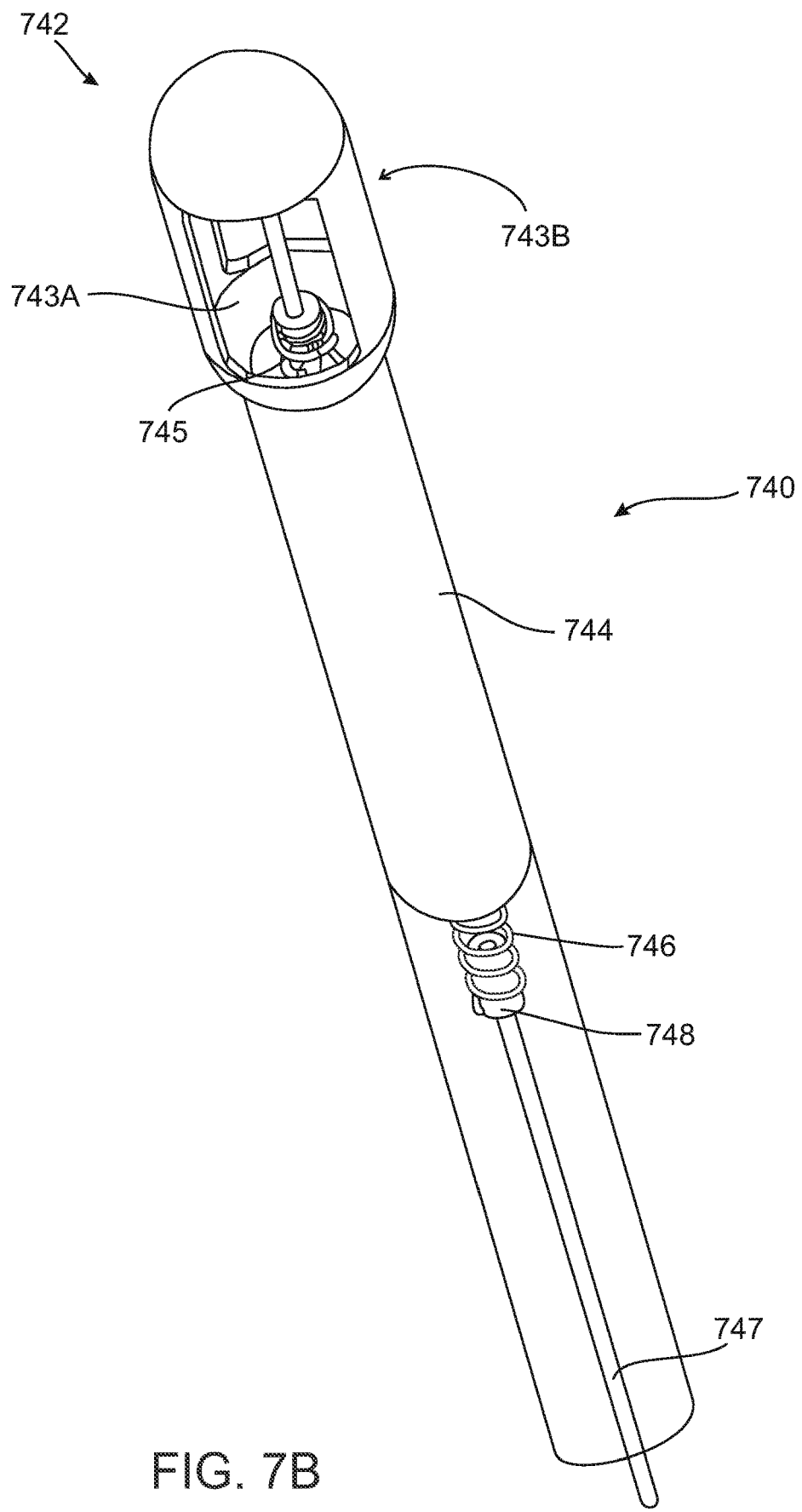

FIG. 7B is a perspective view of the cleaning device of FIG. 7A. Colon cleaning device head 742 has two windows 743A-B, coaxially arranged relative to spring 746 and/or to device 740. To more clearly show spring 746 and coupling location 748, the proximal portion of tube 744 has been removed from the illustration.

FIG. 8A is a perspective view of the cleaning device of FIG. 7A, illustrating the direction of applied torque 802 through rod 747 for rotation of spring 746, as would be provided, for example, by an external motor. Optionally, torque is applied in a direction that helps to transport matter away from the colon by the rotational motion of the helically arranged coils of the spring. Forward and/or reverse motion may also be applied.

FIG. 8B is a cross sectional perspective view of the cleaning head of FIG. 7A, illustrating the direction of applied torque 802.

FIG. 8C is a cross sectional side view of the cleaning head of FIG. 7A.

FIG. 8D is a cross sectional front view of the cleaning head of FIG. 7A.

FIG. 8E is a cross sectional top view of the cleaning head of FIG. 7A.

Reference is now made to an exemplary colon cleaning system 900, in accordance with exemplary embodiments of the present invention. System 900 may contain different possible combinations of one or more embodiments described hereinabove.

System 900 contains one or more optional components:

A waste receptacle 902 for storing removed fecal matter and/or fluids. An optional suction is in fluid communication with receptacle 902 for active transport of waste out of the colon. Receptacle 902 is in fluid communication with cleaning device 914, for example, by one or more material outlet tubes.

A cleaning fluid source 904 for providing fluid for cleaning the colon. Fluid source 904 is in fluid communication with jethead 906, for example, by one or more tubes.

Optionally, an emulsion formation element 924 is in fluid communication with fluid source 904. Optionally, emulsion element 924 is in fluid communication with jethead 906, for example, located between source 904 and jethead 906. Emulsion element 924 mixes gas bubbles into the cleaning fluid to form the emulsion, optionally according to one or more preselected gas bubble parameters. Gas may be obtained from room air and/or from a canister. Optionally, the emulsion is injected into the colon segment through jethead 906, for example, as described herein. Additional details of emulsion formation element 924 are described with reference to FIG. 11.

A torque and/or power source 908 for providing power for moving components located inside the colon, for example, a motor.

A controller 910 to at least control one or more functions of waste receptacle 902, power source 908, cleaning fluid source 904, a colonoscope 912, emulsion element 924, and/or other components described herein. Controller 910 may provide for automatic (software and/or hardware based) and/or manual control.

Optionally, colonoscope 912 is an off-the-shelf colonoscope, for example, commonly used by gastro-intestinal physicians to perform colonoscopies.

One or more components may be integrated into a workstation, for example, receptacle 902, power source 908, fluid source 904 and/or controller 910. The workstation may attach to the cleaning device using one or more tubes and/or cables, for example, as described hereinabove.

Additional details of exemplary components and/or workstation are described, for example, in International Patent Application Publication No. WO 2011/158232.

Optionally, colon cleaning device 914 is slidably coupled to colonoscope 912 using a linear actuator 916, for example, as described hereinabove and/or with reference to FIGS. 5A-5D. Optionally, jethead 906 is coupled to the partial circumference of colonoscope 912, for example, as described hereinabove and/or with reference to FIGS. 6A-6D. Optionally, the head of cleaning device 914 contains one or more disassembly elements 918, for example, as described hereinabove and/or with reference to FIGS. 1, 2A-2F, 3 and/or 4A-4D. Optionally, an actuating mechanism 922 (e.g., as described hereinabove and/or with reference to FIG. 1) actuates disassembly element 918 to perform sweeping displacement inside the cleaning device head, so that disassembly element 918 rotates around the longitudinal axis of the cleaning device head to slice through the fecal matter. Optionally, device 914 contains one or more shredding springs 920, for example, as described hereinabove and/or with reference to FIGS. 7A-7B and/or 8A-8E.

In use, colonoscope 912 coupled to cleaning device 914 is advanced into the colon through the anal sphincter. Alternatively, only device 914 is advanced. Optionally, the physician selected the position of device 914 relative to colonoscope 912, by using linear actuator 916. Fluid from source 904 is injected into the colon by openings on jethead 906. Fecal matter enters device 914 through openings. Optionally, disassembly element 918 slices the fecal matter at the distal end of device 914 into smaller pieces. The sliced fecal matter is transported proximally (using optional suction) and is optionally further shredded into smaller pieces by spring 920. The ground up fecal matter is removed out of the body and into receptacle 902.

Figure 9:
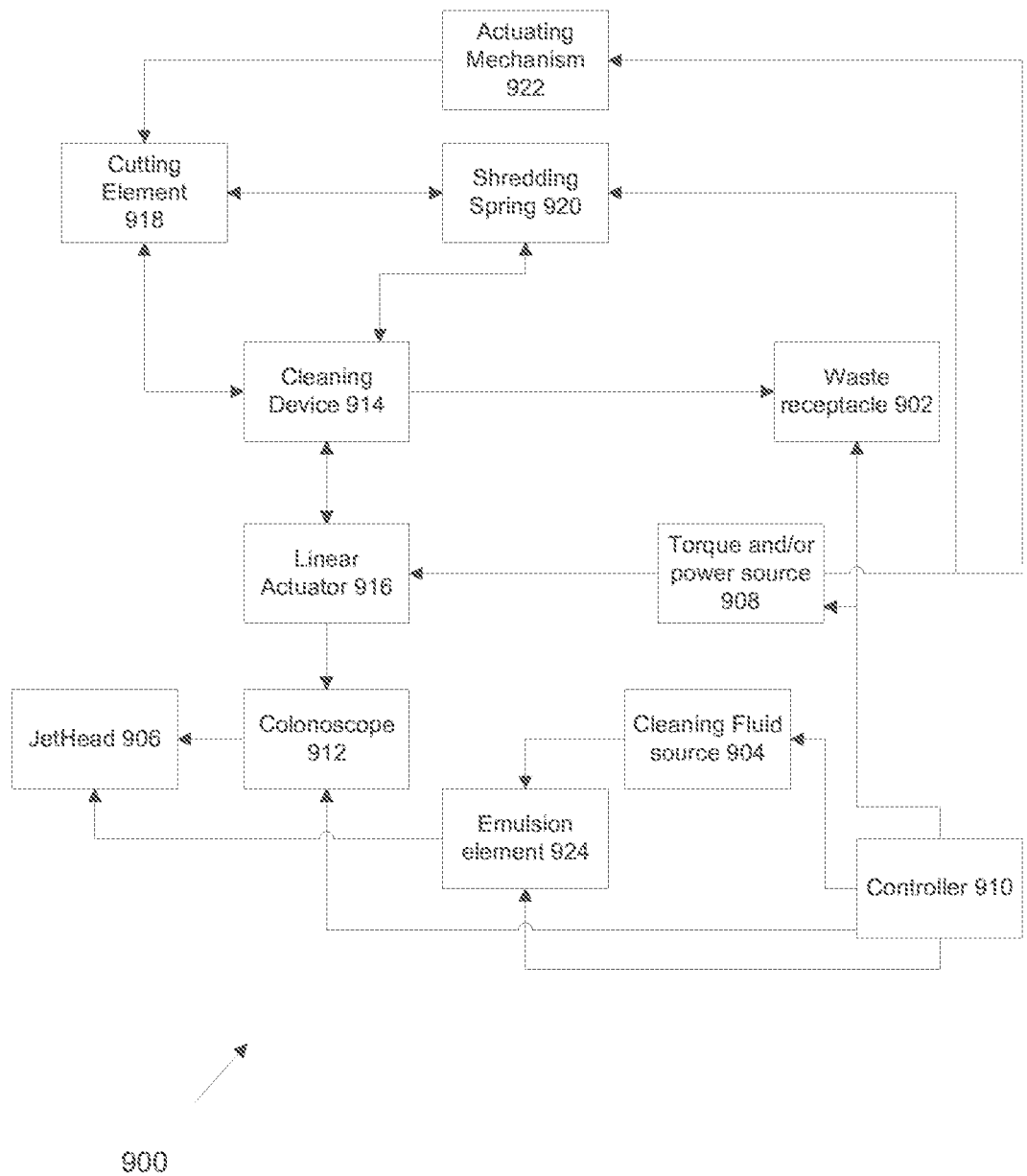
FIG. 9 is an exemplary colon cleaning system, in accordance with exemplary embodiments of the present invention.
Figure 10:
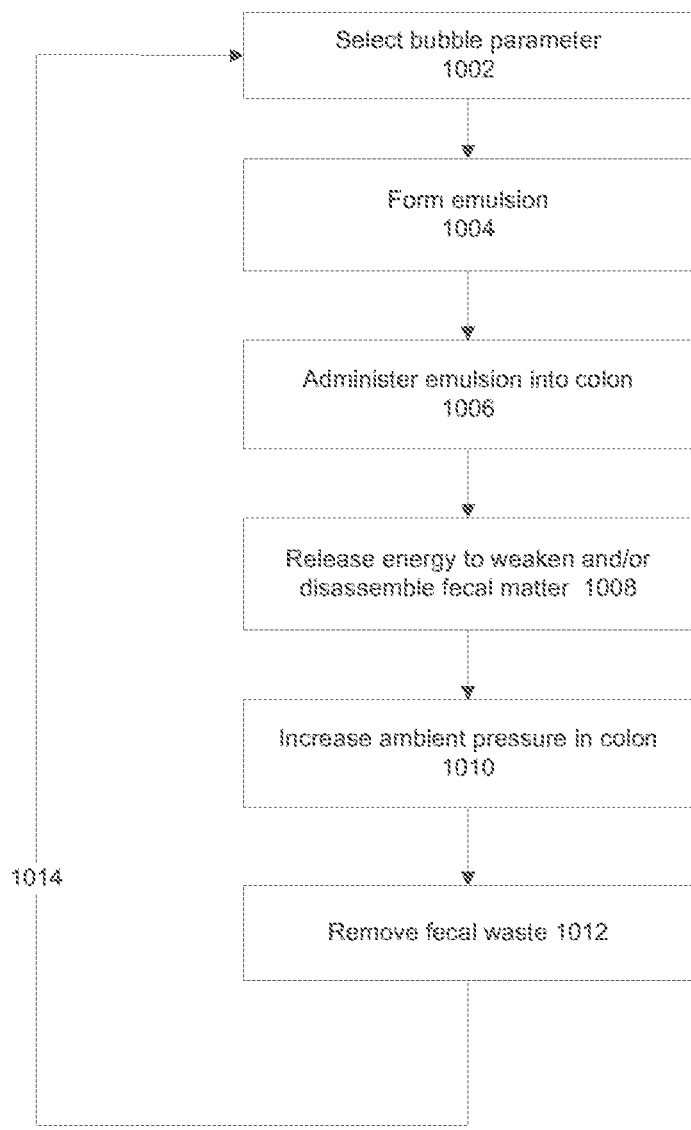
FIG. 10 is a method of cleaning the colon by administration of an emulsion of cleaning fluid and gas bubbles, in accordance with exemplary embodiments of the present invention.
Figure 11:
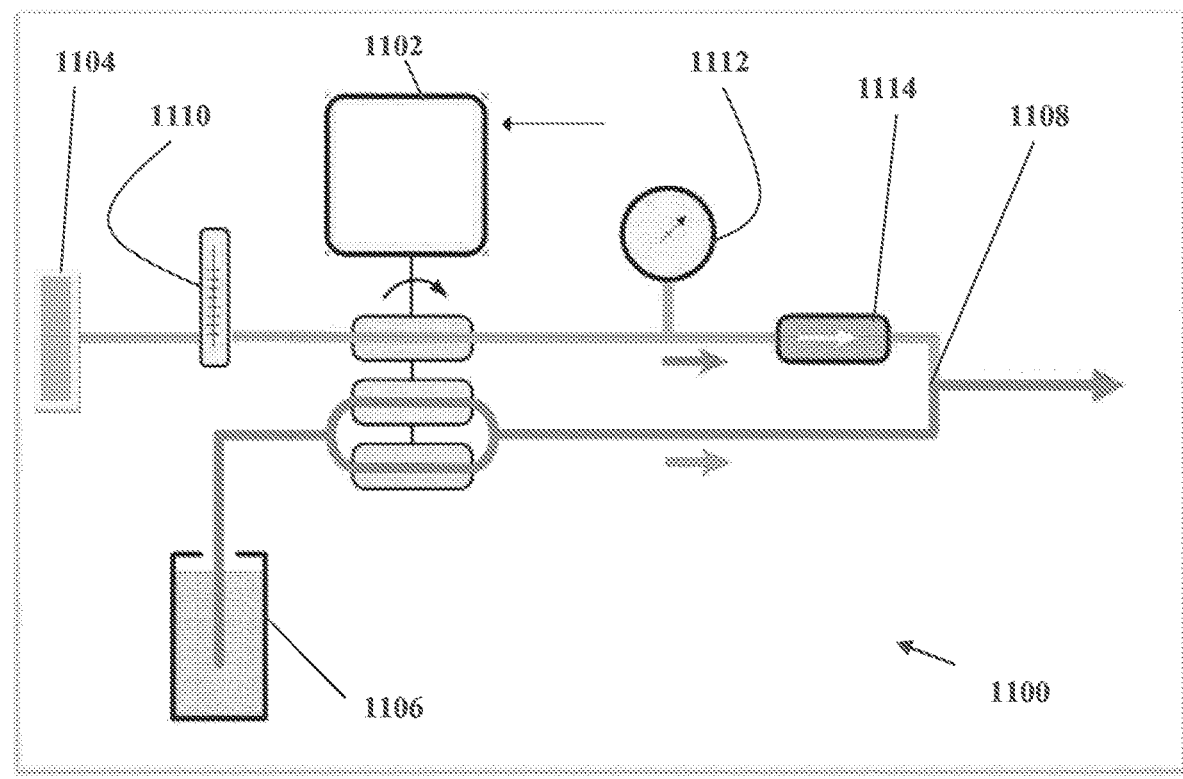
FIG. 11 is a schematic of a system for generating an emulsion of cleaning fluid and gas bubbles in accordance with exemplary embodiments of the present invention.

Reference is now made to FIG. 10, which is a method of cleaning a colon segment of a patient by administration of an emulsion, in accordance with exemplary embodiments of the present invention. Reference is also made to FIG. 11, which is a schematic of an exemplary system 1100 for generating the emulsion of the method of FIG. 10, in accordance with exemplary embodiments of the present invention. FIG. 11 is an exemplary implementation of emulsion element 924 of FIG. 9. Optionally, the emulsion improves disassembly of fecal matter in the colon segment, as compared to disassembly with cleaning fluid without the gas bubbles. Alternatively or additionally, gas released from the bubbles of the emulsion reduces or prevents leakage of waste from the anal sphincter. The gas may direct the waste for removal through a removal tube, instead of leaking. Optionally, the method is carried out and/or the system for generating the emulsion is integrated with, for example, colon cleaning system 900 described with reference to FIG. 9.

System 1100 has a flow control mechanism 1102 for controlling flows of a gas source 1104 and a liquid source 1106. Optionally, the gas and liquid flow separately through mechanism 1102, mixing at a downstream location 1108 to form the emulsion, for example, where the gas and liquid tube combine into a single tube. Mechanism 1102 is, for example, a peristaltic pump, for example, model WT600-2J available from Baoding Longer Precision Pump Co., Ltd.™.

Optionally, an air flow meter 1110 generates a signal indicative of the rate of air flow through the air tube.

Optionally, an air pressure sensor 1112 generates a signal indicative of the pressure in the air flow tube.

Optionally, a one way valve 1114, for example a check valve, is in fluid communication with the air tube before mixing location 1108. Valve 1114 may help ensure that water does not enter the air tube at a location other than mixing location 1109.

Additional exemplary systems for mixing gas and liquid may be found, for example, in WO 2011/158232.

Optionally, at 1002, one or more bubble parameters are preselected, for example, manually by the physician and/or automatically by software. Examples of parameters include:

Type of gas within the bubble: for example, air, carbon dioxide, or other gases safe for injection inside a patient. Carbon dioxide gas may ease patient discomfort associated with the procedure.

Average size and/or distribution size of bubbles. For example, a large bubble size may be selected so that the bubbles float to the surface of the cleaning fluid and burst at the surface. For example, an average size of about 0.1 mm to about 1 mm, or about 0.01 mm to about 0.1 mm, or other sizes. The energy from the burst may disassemble the fecal matter, and/or at least structurally weaken the fecal matter, such as by making tiny holes and/or cracks in the fecal matter. The released gas increases the pressure inside the colon. In another example, a small bubble size may be selected (e.g., microbubbles) so that the bubbles dissolve within the cleaning fluid. For example, about 1-1000 nanometers, or about 1 to 100 micrometers, or other smaller, intermediate or larger sizes. The bubble size may relatively reduce friction between the emulsion and pipes delivering the emulsion from an external reservoir to the colon segment. The reduced friction may allow relatively smaller pipes to be used as compared with pipes delivering cleaning fluid without the gas bubbles.

Ratio of gas bubbles to cleaning fluid, for example, gas volume to cleaning fluid volume, number of gas bubbles per unit of cleaning fluid, or other ratios.

Optionally, at 1004, the emulsion is formed from the cleaning fluid and the selected gas. Optionally, the emulsion is formed with gas bubbles according to the preselected bubble parameters. Control is performed, for example, by controlling the rate of peristaltic pump 1102, the diameter of the air flow tube, liquid tube and/or patient insertion tube (delivering the emulsion), the gas pressure, and/or other parameters.

At 1006, the emulsion is administered into the colon segment. Optionally, the emulsion is injected towards fecal matter inside the colon segment. Alternatively or additionally, the emulsion is administered within the lumen of the colon segment without being specifically targeted towards feces.

At 1008, energy released by the bubbles within the emulsion disassembles the fecal matter. For example, bursting bubbles send shock waves that disassemble the fecal matter and/or weaken the structure of the fecal matter so that the fecal matter may be more easily disassembled.

Optionally, at 1010, gas released from the bubbles into the lumen of the colon segment increases the ambient pressure of the colon. Optionally, the colon is insufflated by the released gas. The operator of the colonoscope and/or cleaning device may visualize the wall of the insufflated colon segment.

Optionally, at 1012, the disassembled fecal matter is removed from the colon segment. Optionally, the fecal matter is removed from the colon segment by a tube connected to a vacuum source.

Optionally, the increase in ambient pressure within the colon segment (block 1010) is detected by a sensor coupled to a colon cleaning device inside the colon segment. Optionally, the increase in pressure automatically triggers activation of the vacuum source so that waste is automatically removed. In this manner, the visual field of the operator may increase as the colon is cleaned.

Alternatively or additionally, the increase in ambient pressure within the colon segment helps to reduce leaks of the waste fluid from the anal sphincter. Instead, the waste fluid may be removed through the outlet tube. The selective removal of waste through the tube may be caused by the higher pressure gradient between the colon segment and vacuum source over the pressure gradient between the colon segment and room pressure.

Figure 12:
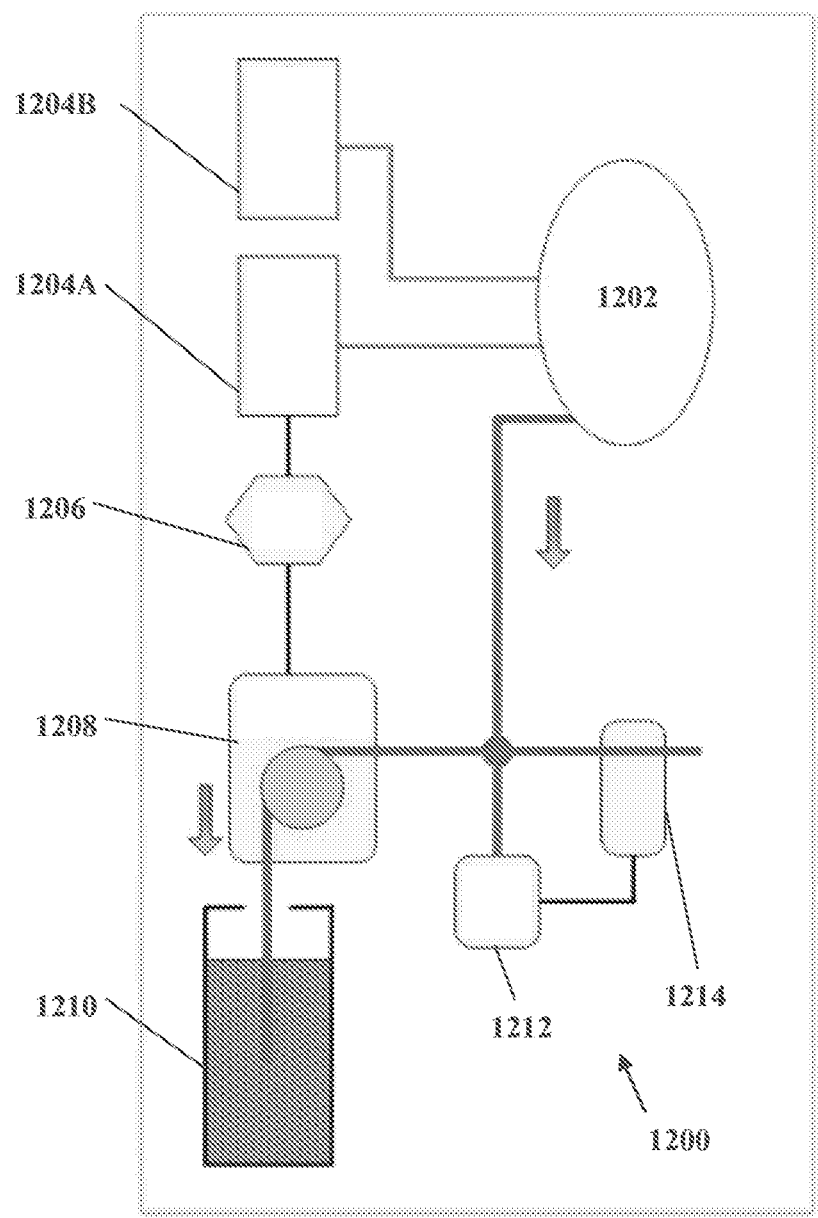
FIG. 12 is a schematic of an exemplary system for controlled removal of waste by suction, in accordance with exemplary embodiments of the present invention.

Attention is now diverted to FIG. 12, which is an exemplary system 1200 for controlled removal of matter from a patient 1202 (direction shown by the arrows), in accordance with exemplary embodiments of the present invention. One or more pressure sensors 1204A-B generate signals (electrical and/or mechanical) indicative of pressure within the colon segment of patient 1202, for example, the ambient gas pressure. A driver 1206 receives the signals generated by sensor 1204 and controls a suction source 1208 in response to the gas pressure. For example, if the gas pressure is above a safe threshold, vacuum source 1208 is activated to removal matter from the colon segment to reduce the pressure. Matter is removed into optional container 1210. Suction source 1208 is, for example, a peristaltic pump, for example, model WT600-2J available from Baoding Longer Precision Pump Co., Ltd.™.

An optional vacuum sensor 1212 generates signals (electrical and/or mechanical) indicative of the vacuum pressure within the matter removal tubing. Sensor 1212 is in communication with an optional valve 1214, for example, a pinch valve that acts as a safety control. For example, if sensor 1212 senses that the vacuum pressure is higher than a safe threshold, pinch valve 1214 opens to relieve the vacuum pressure and bring the pressure back to the safe level.

Additional examples of systems and methods for automatically detecting and controlling the pressure within the colon segment may be found, for example, in WO 2011/158232.

Referring now back to FIG. 10, optionally, at 1014, the process is repeated. Optionally, the process is adjusted. For example, the bubble selection parameters (block 1002) may be adjusted according to the stage of the procedure and/or fecal consistency. For example, different bubble parameters may deliver varying amount of energy to break down fecal matter with varying hardness. In another example, a first bubble parameter may be selected to inflate the colon, and a second parameter may be selected to maintain the insufflation of the colon.

It is expected that during the life of a patent maturing from this application many relevant colon cleaning devices and/or colonoscopes will be developed and the scope of the terms colon cleaning device and colonoscopes are intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this present invention may be presented in a range format. It should be understood that the description in range format is merely for convenience and brevity and should not be construed as an inflexible limitation on the scope of the present invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the present invention, which are, for clarity, described in the context of separate embodiments, may also be provided in combination in a single embodiment. Conversely, various features of the present invention, which are, for brevity, described in the context of a single embodiment, may also be provided separately or in any suitable subcombination or as suitable in any other described embodiment of the present invention. Certain features described in the context of various embodiments are not to be considered essential features of those embodiments, unless the embodiment is inoperative without those elements.

Although the present invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for colon cleaning comprising:
  a jethead having an inner surface shaped for fitting partially around the circumference of a distal end portion of a colonoscope by attaching said jethead to said colonoscope, wherein said distal end portion of said colonoscope is a leading end of said colonoscope when said colonoscope is being inserted through an anal sphincter of a patient;
  a plurality of jets located within the jethead, the jets arranged to spray a fluid into a colon, the plurality of jets in fluid communication with an external source of the fluid through at least one tube;

a gas inlet for supplying pressurized gas into the jethead; and a material output tube through which liquid and fecal matter are removed, the material output tube having an inner surface shaped for fitting a portion of the colonoscope, at a location proximal to the jethead;

wherein a distal portion of the jethead is angled towards the center of the colonoscope such that a thickness of said jethead at an edge of said colonoscope at said distal end portion is smaller than a thickness of said jethead at a proximal edge of the jethead on said colonoscope, said angled distal portion is configured to ease an insertion of said colonoscope fitted with said device through said anal sphincter; and wherein the device is sized and shaped so that the combined colonoscope and device is displaceable along the colon of a patient.

2. The device of claim 1, wherein the inner surface of the jethead is shaped for fitting around about 150-180 degrees of the distal end portion.

3. The device of claim 1, wherein the plurality of jets are in fluid communication with one another and with the external source through a manifold in the jethead.

4. The device of claim 1, wherein said gas inlet is for supplying pressurized gas to inflate the colon.

5. The device of claim 1, wherein the at least one tube in fluid communication with the external source of the fluid, is an add-on to a colonoscope, the at least one tube being sized to fit into the colon through an anal sphincter of a patient when coupled to the colonoscope.

6. The device of claim 1, further comprising a band attaching said jethead to said colonoscope.

7. The device of claim 1, wherein said material output tube is attached to a first side of the surface circumference of said colonoscope, and wherein said jethead is attached to a second side of the surface circumference of said colonoscope, opposing said first side of the circumference of said colonoscope.

8. The device of claim 1, wherein an arc length of said inner surface of said jethead is selected according to at least one of a number of jets of the plurality of jets, and a position of said plurality of jets.

\* \* \* \* \*